United States Patent
Schoenbach et al.

(10) Patent No.: US 8,682,426 B2
(45) Date of Patent: Mar. 25, 2014

(54) DELIVERY DEVICE, SYSTEM, AND METHOD FOR DELIVERING NANOSECOND PULSED ELECTRIC FIELDS

(75) Inventors: Karl H. Schoenbach, Norfolk, VA (US); Stephen J. Beebe, Norfolk, VA (US); Tammo Heeren, Aliso Viejo, CA (US); Juergen F. Kolb, Norfolk, VA (US); Shu Xiao, Norfolk, VA (US); Richard Blomgren, Dacula, GA (US); Roelof Trip, Suwanee, GA (US)

(73) Assignee: Old Dominion Research Foundation, Norfolk, VA (US)

( * ) Notice: Subject to any disclaimer, the term of this patent is extended or adjusted under 35 U.S.C. 154(b) by 197 days.

(21) Appl. No.: 12/418,864

(22) Filed: Apr. 6, 2009

(65) Prior Publication Data

US 2009/0299417 A1    Dec. 3, 2009

Related U.S. Application Data

(60) Provisional application No. 61/042,948, filed on Apr. 7, 2008.

(51) Int. Cl.
*A61N 1/04* (2006.01)

(52) U.S. Cl.
USPC .............. 607/2; 607/50; 607/115; 607/148; 600/372; 600/373

(58) Field of Classification Search
USPC .............. 607/2, 50, 115, 116, 145, 148, 149; 600/372, 373; 128/907; 606/44; 604/20, 21; 435/173.6
See application file for complete search history.

(56) References Cited

U.S. PATENT DOCUMENTS

| | | | |
|---|---|---|---|
| 4,907,601 A * | 3/1990 | Frick | 607/115 |
| 5,389,069 A * | 2/1995 | Weaver | 604/21 |
| 5,660,836 A | 8/1997 | Knowlton | |
| 5,674,267 A | 10/1997 | Mir et al. | |
| 6,277,116 B1 * | 8/2001 | Utely et al. | 607/102 |
| 6,377,854 B1 | 4/2002 | Knowlton | |
| 6,632,193 B1 | 10/2003 | Davison et al. | |
| 7,412,284 B2 * | 8/2008 | Hofmann | 604/21 |
| 7,570,992 B2 * | 8/2009 | Nolan et al. | 604/21 |
| 7,824,394 B2 * | 11/2010 | Manstein | 606/9 |

(Continued)

OTHER PUBLICATIONS

Schoenbach, Karl H. et al., "Intracellular Effect of Ultrashort Electrical Pulses", Bioelectromagnetics 22:440-448, 2001.

Buescher, E. Stephen et al., "Effects of Submicrosecond, High Intensity Pulsed Electric Fields on Living Cells—Intracellular Electromanipulation", IEEE Transactions on Dielectrics and Electrical Insulation, vol. 10, Issue 5, pp. 788-794, Oct. 2003.

(Continued)

*Primary Examiner* — Carl H Layno
*Assistant Examiner* — Eugene Wu
(74) *Attorney, Agent, or Firm* — Novak Druce Connolly Bove + Quigg LLP

(57) ABSTRACT

A medical instrument for delivering electrotherapy to tissue that includes an outer support member having a ground plate at a distal end of the outer support member, and a protrusive element having a tip that extends beyond the ground plate. A portion of the protrusive element proximate the ground plate can act as an electrical insulator and a portion of the protrusive element proximate the distal end of the protrusive element can include a first electrode. The protrusive element can be designed to penetrate into tissue below a tissue surface while a tissue contacting surface of the ground plate rests against the tissue surface. Also disclosed are systems incorporating the medical instrument and methods of electrotherapy to subsurface tissue using the medical instrument.

17 Claims, 20 Drawing Sheets

(56) References Cited

U.S. PATENT DOCUMENTS

| | | | |
|---|---|---|---|
| 2003/0153960 A1* | 8/2003 | Chornenky et al. | 607/72 |
| 2004/0098074 A1* | 5/2004 | Erickson et al. | 607/117 |
| 2007/0066959 A1* | 3/2007 | Seward | 604/20 |
| 2008/0228244 A1 | 9/2008 | Pakhomov et al. | |

OTHER PUBLICATIONS

White, Jody A. et al., "Stimulation of Capacitive Calcium Entry in HL-60 Cells by Nanosecond Pulsed Electric Fields", The Journal of Biological Chemistry, vol. 279, No. 22, pp. 22964-22972, May 28, 2004.

\* cited by examiner

Scanning Line (z=0.6 cm)

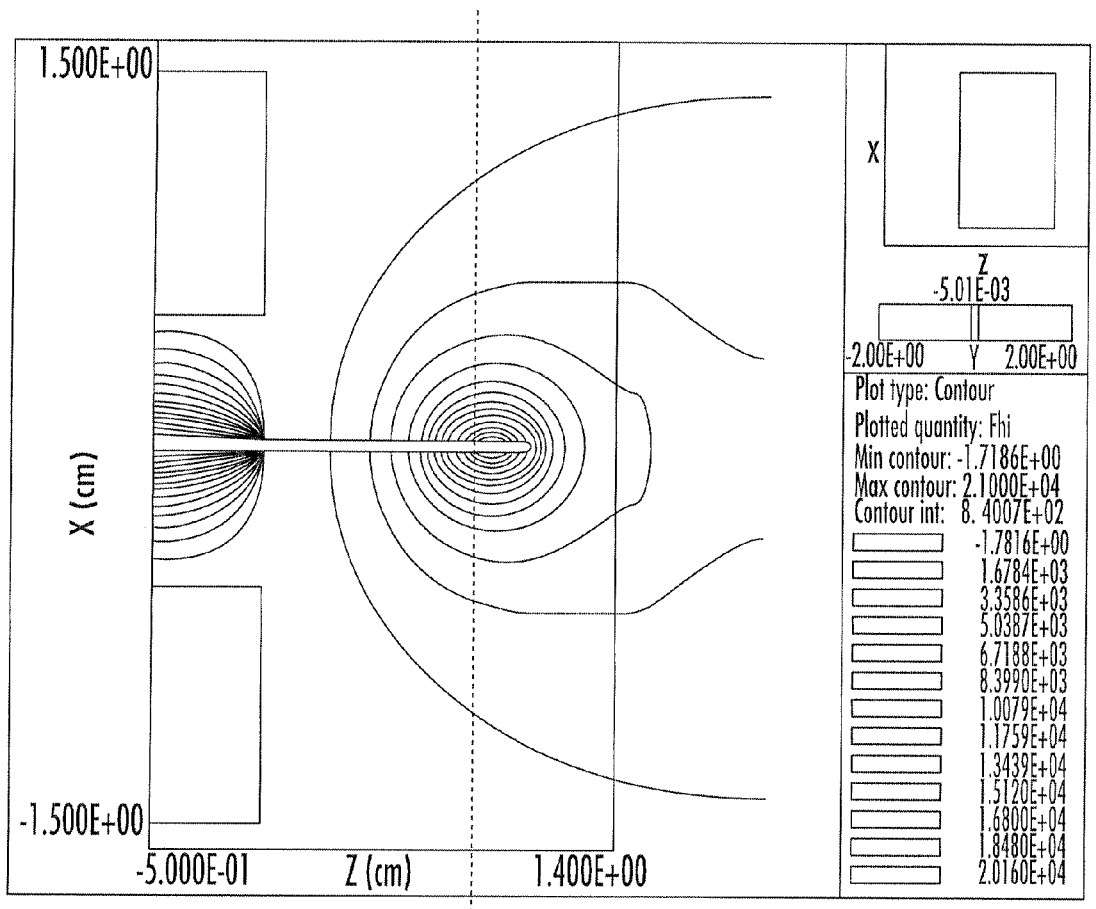
Scanning Line
(z=0.8 cm) FIG. 16A
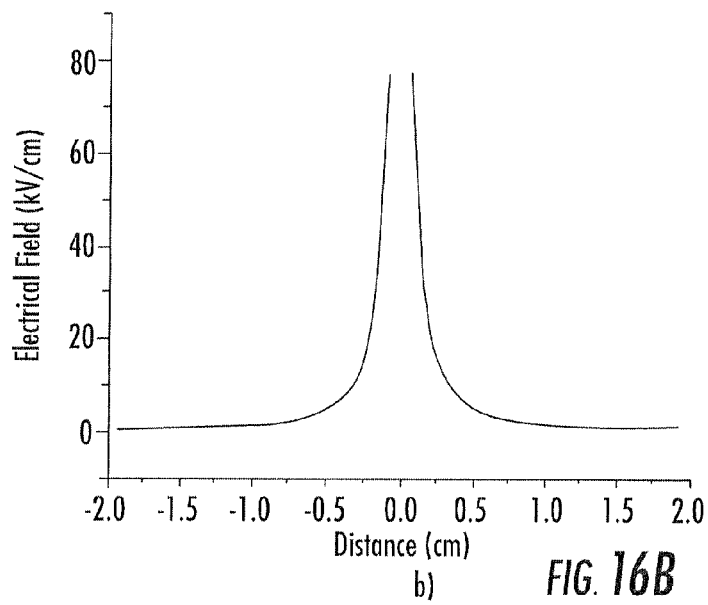
b) FIG. 16B

Scanning Line (z=0.8 cm)

DELIVERY DEVICE, SYSTEM, AND METHOD FOR DELIVERING NANOSECOND PULSED ELECTRIC FIELDS

CROSS-REFERENCE TO RELATED APPLICATIONS

This application claims priority to U.S. Provisional Patent Application No. 61/042,948 filed Apr. 7, 2008, the entirety of which is hereby incorporated by reference.

FIELD OF THE INVENTION

The present invention relates to medical instruments, systems and methods for delivering electrotherapy to tissue.

BACKGROUND

Nanosecond-pulsed electric fields (nsPEF) applied to tissue have been shown to impart low energy in the tissue leading to very little heat production. The ability of nsPEF to penetrate into the cell to permeabilize intracellular organelles is known. (See Schoenbach et al., 2001, *Bioelectromagnetics* 22, 440-448; Buescher and Schoenbach, 2003, *IEEE Transactions on Dielectrics and Electrical Insulation* 10, 788-794; White J A, et al., 2004, J Biol Chem. 2004 May 28; 279(22): 22964-72. Epub 2004 Mar. 16.).

The electric fields of nsPEFs differ from those commonly used for classical electroporation in multiple ways. First, the durations range from 1 microsecond to 200 picoseconds with rise times from 50 nanoseconds to 50 picoseconds. Second, nsPEFs can have a 20-fold larger amplitude, such as about 1 kV/cm to megavolts/cm or more. These differences in pulse parameters are believed to allow nanosecond-width pulses to penetrate into cells and electroporate organelle membranes in addition to the plasma membrane. Two separate factors are believed to produce the intracellular penetration. First, the rise time of the nsPEFs is faster than the charging time of the plasma membrane, resulting in penetration of the electric field into the cell interior. This internal field generates a current that charges the outer plasma membrane. Most cells exhibit a charging time constant of about 100 nanoseconds. This is for cells in a suspension, and would be longer for tissues. After this charging time, the resulting charge redistribution will screen out the electric field from the cell interior unless the field strength within the plasma membrane has become large enough to generate pores that provide the second mechanism for intracellular penetration.

Second, if the potential difference across the membrane exceeds about 1.6 volts, the formation of nanopores occurs within nanoseconds or less. This allows conduction current to enter the cell during the time that the pores are open. For the large field strengths used for nsPEFs, all of the molecules and organelles inside the cell will be exposed to the imposed electric field for up to hundreds of nanoseconds during each pulse due to the timing of the charging current and the open time of the field-induced pores. By applying multiple pulses, the total time of field exposure can be increased in proportion to the number of pulses applied.

SUMMARY

The present invention discloses instruments, systems and methods for delivering electrotherapy to tissue. In particular, the instruments, systems and methods of the present invention are capable of delivering electrotherapy to tissue without imparting substantial electrical or thermal damage to the surface of the tissue, e.g., the skin.

In one embodiment, the invention can be a medical instrument for delivering electrotherapy to tissues at a controllable, localized depth without the electrical field used for the electrotherapy causing damage to the surface skin. The medical instrument can include an outer support member having a ground plate at a distal end of the outer support member and a protrusive element having a tip that extends beyond the ground plate. The protrusive element can include a conducting material. A portion of the protrusive element proximate the ground plate can be an electrical insulator and a portion of the protrusive element proximate the distal end of the protrusive element can include a first electrode. The protrusive element can be designed to penetrate into tissue below the tissue surface while a tissue contacting surface of the ground plate rests against the tissue surface. The protrusive element can extend from within a perimeter of the ground plate.

In some embodiments, at least a portion of the tissue-contacting surface of the ground plate is not itself, and is not coated with, an electrically insulating material and at least a portion of the first electrode is not itself, and is not coated with, an electrically insulating material. The entire tissue contacting surface of the ground plate can be free of any electrically insulating coating. The protrusive element, the ground plate, or both can be removable.

The tissue contacting surface of the ground plate can be symmetric along at least one axis passing through and perpendicular to a longitudinal axis of the protrusive element. The ground plate can have a tissue contacting surface that is symmetric along at least two axes passing through and perpendicular to a longitudinal axis of the protrusive element. In some embodiments, the ground plate can have a tissue contacting surface that is symmetric along two orthogonal axes passing through and perpendicular to a longitudinal axis of the protrusive element.

The protrusive element can include a needle that can be made of an electrically conductive material. The needle can be coated with an electrical insulator. The portion of the protrusive element proximate the ground plate that acts as an electrical insulator can be at least about 0.15 cm in length, at least about 0.2 cm in length, at least about 0.3 cm in length or at least about 0.5 cm in length.

The first electrode can be 4 cm or less in length. A tissue contacting surface of the ground plate can be a ring and the protrusive element can extend from the center of the ring.

The medical instrument can also include one or more additional protrusive elements having sharp tips that extend beyond the ground plate, wherein a portion of each additional protrusive element proximate the ground plate can act as an electrical insulator and a portion of each additional protrusive element proximate the distal end of each additional protrusive element can include additional first electrodes. Each additional protrusive element can be designed to penetrate into tissue below a tissue surface while the ground plate rests against the tissue surface. In embodiments where the medical instrument includes one or more additional protrusive elements, the first electrode and at least one additional first electrode can be wired such that the first electrode and at least one additional first electrode can be independently energized at the same or different voltages. The medical instrument can include at least two protrusive elements that can extend from within a perimeter of the ground plate.

In another embodiment, the invention can be a system for delivering electrotherapy to tissue. The system can include the medical instrument for delivering electrotherapy to tissue, described above, and a power supply electrically coupled to the ground plate and the first electrode. The power supply can generate electrical signals to the medical instrument for delivering electrotherapy to tissue.

The power supply can include a pulse generator. The pulse generator can include a nanosecond pulsed electric field (nsPEF) generator.

In another embodiment, the invention can be a method of delivering electrotherapy to subsurface tissue of a mammalian subject. The method includes inserting the protrusive element of the above-described medical instrument for delivering electrotherapy to subsurface tissue into subsurface tissue where the ground plate can be contacting a tissue surface. The method can include applying one or more nanosecond pulses creating a voltage difference between the ground plate and the first electrode of 1 to 100 kV. The method can also include measuring the skin thickness of the mammalian subject and selecting a medical instrument where the portion of the protrusive element that acts as an insulator is at least as long as the measured skin thickness.

The pulses can be applied to selectively target fiber septae. The pulses selectively targeting fiber septae can be applied to reduce dimpling of the tissue surface.

The nanosecond pulse can be 100 picoseconds to 1 microsecond in duration. The peak power produced between the ground plate and the first electrode can be greater than or equal to about 1 MW. The peak electrical field produced by the pulse can be at least 10 kV/cm. The temperature increase of the surface tissue proximate the first electrode caused by the nanosecond pulsed electric field can be about 1 degree Celsius or less.

These and other embodiments are described in more detail below.

BRIEF DESCRIPTION OF THE DRAWINGS

The invention is described with more particularity below. The scope of this invention may be better understood by referring to the following description taken in conjunction with the accompanying drawings, in which:

FIG. 16(a) is a graph of the conductive phase equal-potential distribution for Example 2; and (b) is a graph of the conductive phase electrical field distribution along the scanning line for Example 2.

DETAILED DESCRIPTION

Figure 1:
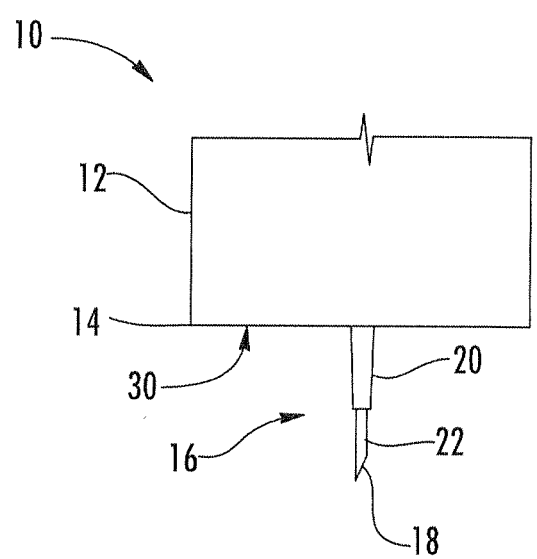
FIG. 1 is a side view of an exemplary medical instrument for delivering electrotherapy to subsurface tissue.

The inventive medical instruments, systems and methods are designed to deliver a nanosecond pulsed electric field (nsPEF) to a controlled volume of target tissue without causing thermal or electrical damage to the surface of the tissue.

As shown in FIGS. 1-7, an exemplary medical instrument 10 for delivering a nanosecond pulsed electric field can include an outer support member 12 having a ground plate 14 at a distal end of the support member 12. The instrument 10 can also include a protrusive element 16 having a sharp tip 18 that extends beyond the ground plate 14. A portion of the protrusive element 16 proximate the ground plate 14 can act as an electrical insulator 20 and a portion of the protrusive element 16 proximate the distal end of the protrusive element 16 can include a first electrode 22. The medical instrument 10 is designed such that the ground plate 14 is designed to rest against the tissue surface 24, e.g., the epidermis, and the tip 18 is designed to penetrate into subsurface tissue 26, e.g., adipose tissue. The tip 18 can be sharp.

The protrusive element 16 can include an electrically conducting material partially or fully coated with an electrical insulator. The protrusive element 16 can include a needle 28 comprising an electrically conductive material partially or fully coated with an electrical insulator 20. The electrical insulator 20 can be an electrical insulating jacket formed from one or more electrically insulating sheaths or coatings. Exemplary electrical insulators 20 include Parylene, polyimide, fluoropolymers, including polytetrafluoroethylene, such as that sold under the TEFLON mark, and other medically useful coatings. The sheath can be applied using shrink wrapping techniques, conventional techniques for applying liquid coatings, or other known coating techniques, such as vapor deposition. The thickness of the electrical insulator 20 can be about 0.127 mm or less, about 0.0762 mm or less or about 0.0254 mm or less.

Figure 4:
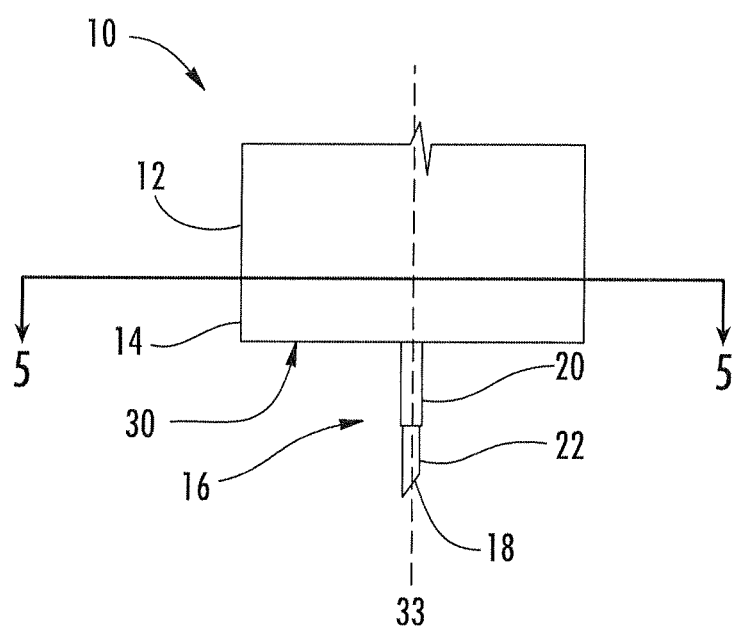
FIG. 4 is a side view of an exemplary medical instrument for delivering electrotherapy, where the electrical insulator forms the majority of the protrusive element and the first electrode is attached to the end of the insulator.
Figure 5:
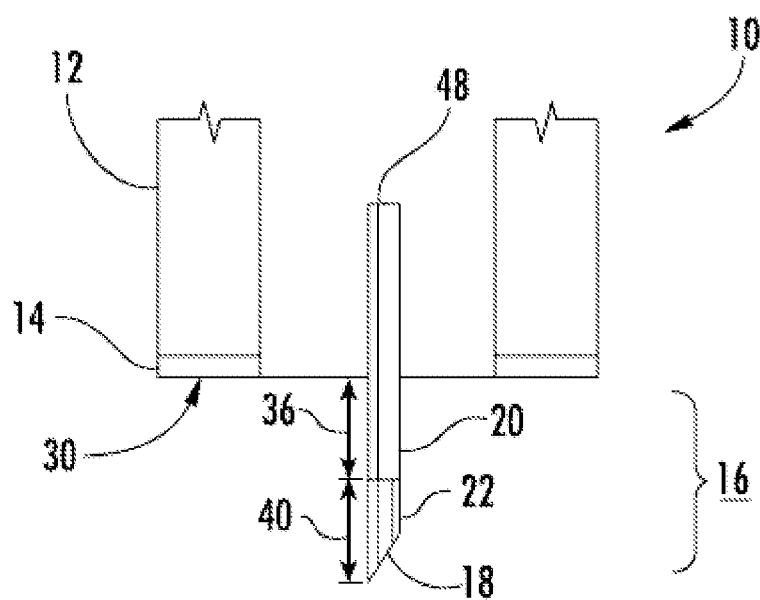
FIG. 5 is a cross-sectional view of the exemplary medical instrument of FIG. 1 take along cut line 5-5 in FIG. 4.
Figure 6:
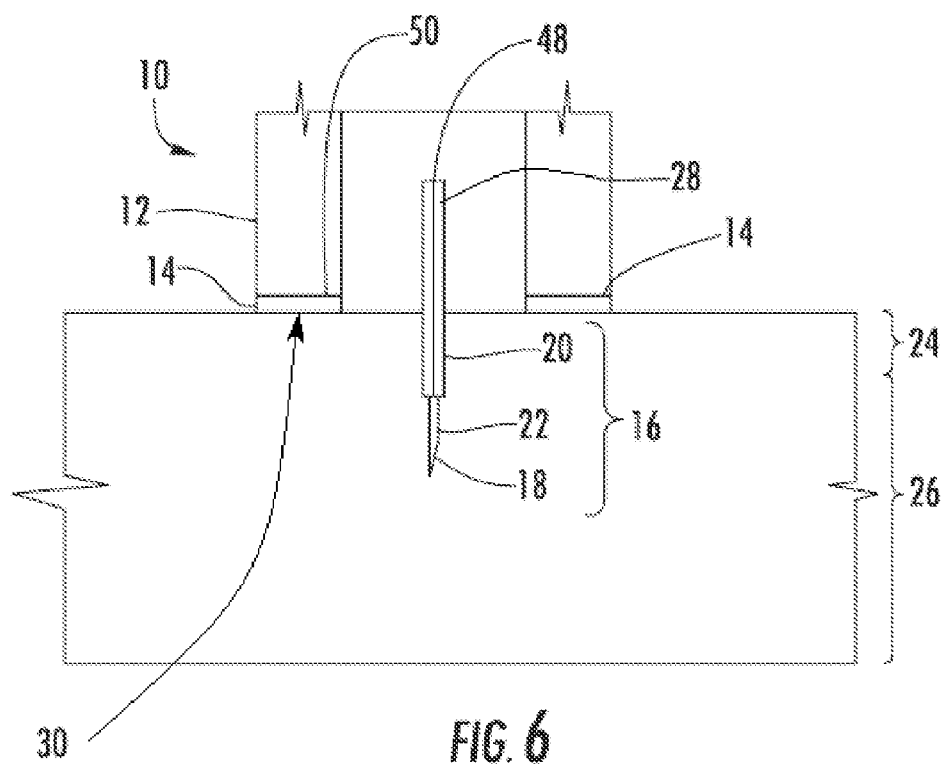
FIG. 6 is the cross-sectional view of the exemplary medical instrument of FIGS. 1-3 where the protrusive element has penetrated the skin and a nanosecond pulsed electric field is ready to be applied.

The electrical insulator 20 can form the majority of the protrusive element and the first electrode 22 can attach to the end of the insulator 20. As shown in FIGS. 4 & 5, the first electrode 22 can be an electrically conductive material coated onto an electrical insulator 20. The first electrode 22 can be electrically conductive material that is attached to the electrical insulator 20.

One of the benefits of the inventive medical instrument 10 and system 34 is that the medical instrument 10 can deliver targeted treatment to a volume of subsurface tissue 26, e.g. subcutaneous tissue, with a nsPEF without causing thermal or electrical damage to the tissue surface 24 or other surrounding tissue. In part, this is possible because, when compared to conventional electroporation, the inventive instrument 10 and system 34 utilize pulses that are generally more than 100 times shorter at a power level that is generally more than 10,000 times larger.

In some embodiments no electrically insulating coating is applied to the ground plate 14. In some embodiments, at least a portion of the ground plate 14 is not coated with an electrically insulating coating. In other embodiments, at least a portion of the first electrode 22 is not coated with electrically insulating material 20. In still other embodiments, at least a portion of the ground plate is not coated with an electrically insulating coating and at least a portion of the first electrode 22 is not coated with electrically insulating material 20.

The electrically insulating material 20 extending along the protrusive element 16 from a point proximate the ground plate 14 can have a length 36 of at least about 0.2 cm, at least about 0.3 cm, at least about 0.4 cm, at least about 0.5 cm, or at least about 0.6 cm. The length 36 of the electrically insulating material 20 can range from 0.1 cm to 2 cm, from 0.15 cm to 1 cm, from 0.15 cm to 0.7 cm, from 0.2 cm to 0.6 cm, or any combination thereof, e.g., 0.1 cm to 0.6 cm.

The electrical field created by the nanosecond pulses is strongest in the tissue immediately surrounding the first electrode 22. Because the first electrode 22 is at an end of the protrusive element 16 beyond the electrically insulating material 20, the first electrode 22 can be at least the length of the electrically insulating material 20 below the tissue surface 24. The amplitude of the electrical field decays rapidly as the distance from the first electrode 22 increases. Thus, the spacing provided by the electrically insulating material 20 can allow the first electrode 22 to deliver nsPEF treatments to a volume of subsurface tissue 26 without causing thermal or electrical damage to the tissue surface layer 24, e.g., the epidermis.

The first electrode 22 can have a cylindrical, needle shape. In such instances, the first electrode may have a diameter 38 of about 1 mm or less, about 0.75 mm or less, about 0.5 mm or less, or about 0.3 mm or less. All other variables being constant, the electric field in the subsurface tissue 26 proximate the first electrode 22 will increase as the diameter 38 of the first electrode 22 decreases.

The protrusive element 16 can be solid or hollow, such as a needle 28. Where the protrusive element 16 is hollow, the hollow cavity within the protrusive element 16 can be connected to a reservoir, as in a hypodermic needle, and used to inject active and inert ingredients to supplement the nsPEF treatments.

The length 40 of the first electrode 22, or exposed length 40 of the first electrode 22 where the protrusive element 16 is a conductive needle 28 coated with an electrically insulating material 20, can be at least about 0.001 cm, at least about 0.01 cm, at least about 0.1 cm, at least about 0.2 cm, at least about 0.3 cm, at least about 0.4 cm or at least about 0.5 cm. The exposed length 40 of the first electrode 22 can be about 4 cm or less, 2 cm or less, 1 cm or less, about 0.5 cm or less, about 0.4 cm or less, about 0.3 cm or less, about 0.2 cm or less, about 0.1 cm or less, about 0.05 cm or less, about 0.01 cm or less, or about 0.001 cm or less. The range of the exposed length 40 of the first electrode 22 can be any combination of the above maximums and minimums, e.g., range from about 0.001 cm to about 0.1 cm.

Figure 7:
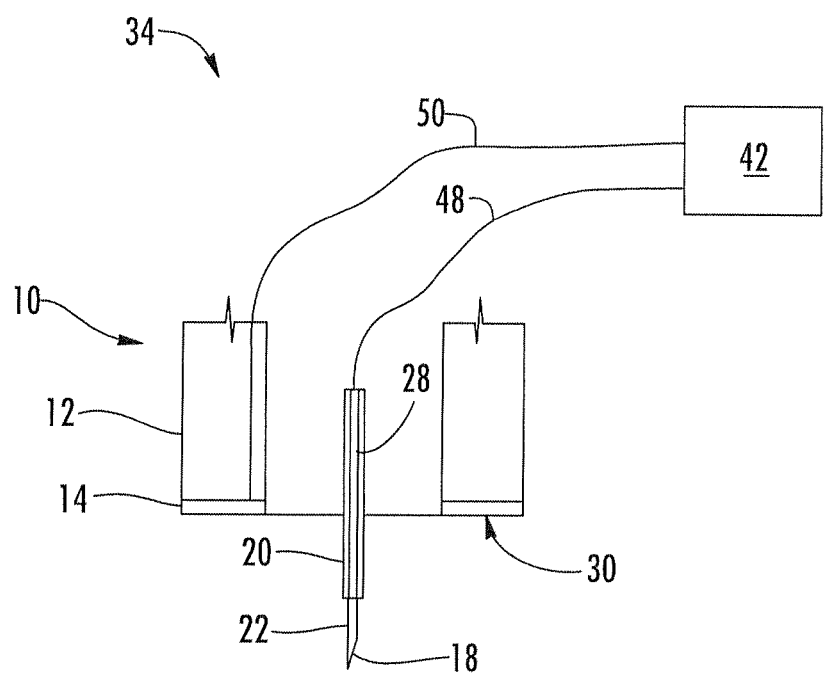
FIG. 7 is a schematic view of an exemplary system for delivering electrotherapy to subsurface tissue that includes an exemplary medical instrument for delivering electrotherapy to subsurface tissue and a power supply electrically couples to the ground plate and the first electrode.

As shown in FIG. 7, the system 34 for delivering electrotherapy to tissue 26 can include a medical instrument for delivering electrotherapy 10 and a power supply 42 that can be electrically coupled to the ground plate 14 and the first electrode 22. A variety of power supplies 42 can be used with the present invention. An exemplary power supply is a pulsed power supply capable of delivering nanosecond high voltage pulses which are imposed across the ground plate 14 and the first electrode 22, to generate electrical fields on the order of 1 to 100 kV/cm. One suitable power supply arrangement for generating nsPEFs together with medical instruments according to the invention is disclosed in U.S. Provisional Patent Application No. 60/895,187 entitled "MODULATION OF NEUROMUSCULAR FUNCTIONS WITH ULTRASHORT ELECTRICAL PULSES" filed on Mar. 16, 2007, which was attached as an appendix to underlying U.S. Provisional Patent Application No. 61/042,948 filed Apr. 7, 2008, the entirety of which is hereby incorporated herein by reference.

As seen in FIG. 7, each electrode 14, 22 can be electrically isolated from one another by having the electrodes 14, 22 connected to separate electrically conductive wires 48, 50 connected to a power supply 42. This allows each electrode 14, 22 to be connected to a different power supply 42, or power supply terminal, and biased differently for maximum versatility. The ground plate 14 can be at a ground potential state or at another potential state, e.g., −12 kV or +12 kV.

The power supply 42 can include a pulse generator capable of producing pulse durations of about 10 microseconds or less, or ranging in duration from about 5 microsecond to about 200 picoseconds, or from about 1 microsecond to about 1 nanosecond, or from about 10 nanoseconds to about 400 nanoseconds, or a range of any combination of pulse durations disclosed herein, e.g., about 1 microsecond to 150 nanoseconds. The nanosecond pulses applied in the associated method can have any of the above-identified ranges.

The electrodes 14, 22 can comprise an electrical conductor that is resistant to corrosion, e.g., stainless steel. The tissue contacting surface 30 of the ground plate 14 and the first electrode 22 can be electropolished or otherwise planarized. Electropolishing removes corners and sharp edges to minimize undesirable corona discharge when large voltages associated with generating nsPEF are applied to the electrodes 14, 22. Polishing in general is used to provide a smoother surface for charges to reside upon and to eliminate sharp edges that focus and enhance the electric field in that region. This results in a reduction of corona discharges.

Figure 8:
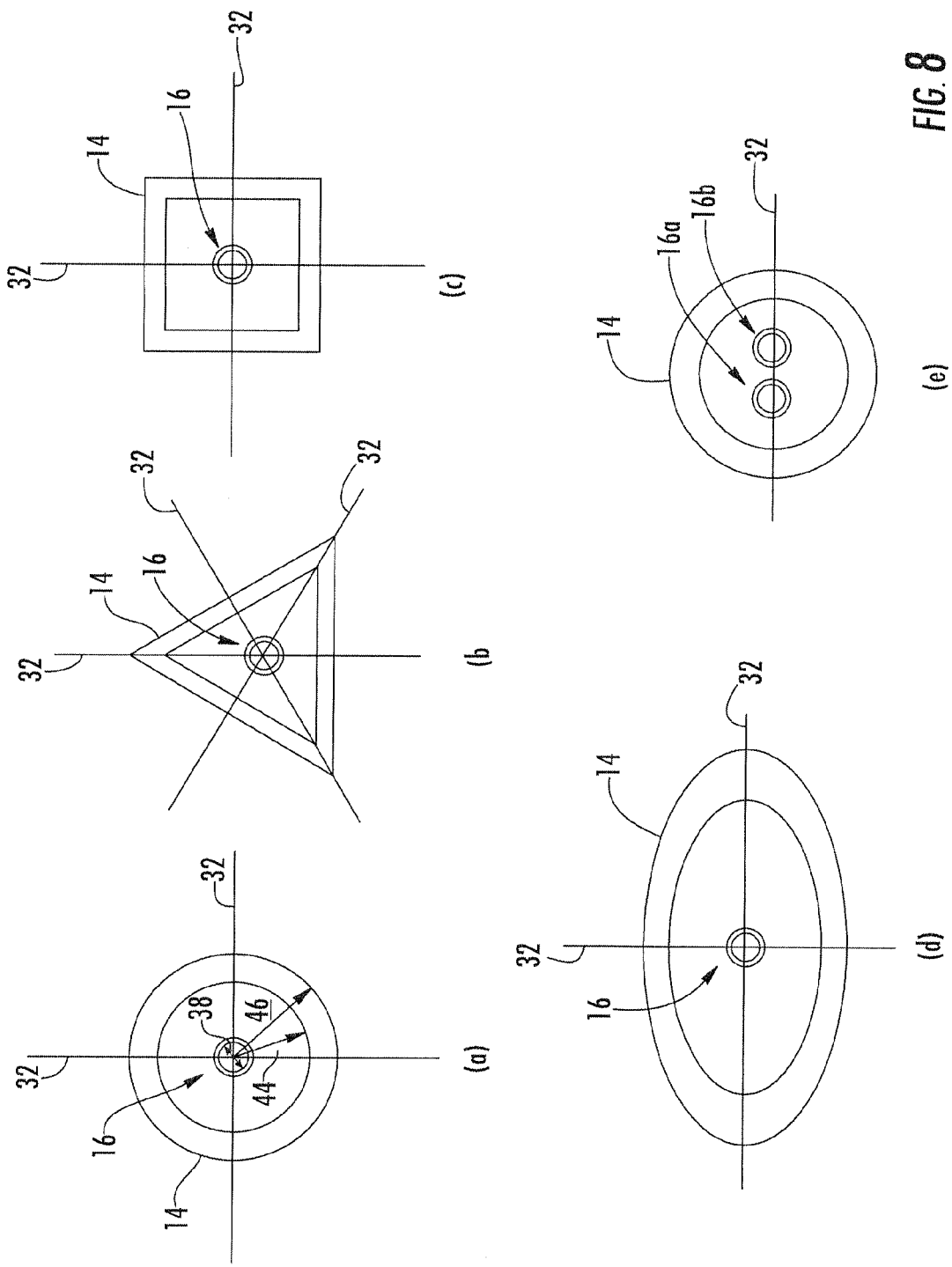
FIGS. 8(a)-(e) are bottom views of several exemplary geometries of the ground plate and the protrusive elements that can be used in the exemplary medical instruments disclosed herein.

As shown in FIGS. 8(a)-(d), the ground plate 14 can have a tissue contacting surface 30 that is symmetrical along at least one axis 32 passing through a longitudinal axis 33 of the protrusive element 16. The ground plate 14 can have a tissue contacting surface 30 that is symmetrical along at least two axes 32 passing through a longitudinal axis 33 of the protrusive element 16. As shown in FIGS. 8(a), (c) and (d), the ground plate 14 can have a tissue contacting surface 30 that is symmetrical along two orthogonal axes 32 passing through a longitudinal axis 33 of the protrusive element 16. It will be appreciated that FIGS. 8(a)-(e) do not show all possible axes of symmetry 32, for examples FIG. 8(c) has at least 4 axes of symmetry passing through a longitudinal axis 33 of the protrusive element. In each of the embodiments described above, the axes of symmetry 32 can pass through the center of the protrusive element 16.

As shown in FIG. 8(e), the medical instrument 10 can include more than one protrusive element 16 disposed within the perimeter of the ground plate 14. Where the medical instrument includes more than one protrusive element, each of the protrusive elements can be wired so that first electrode 22 of each protrusive element 16(a), 16(b) can remain at the same voltage. The first electrode 22 of the more than one protrusive elements 16(a), 16(b) can be wired so that at least two first electrodes 22 can be energized simultaneously or separately at the same or different voltages. As shown in FIG. 8(e), when the medical instrument 10 includes multiple protrusive elements 16, the ground plate 14 can have a tissue contacting surface 30 that is symmetrical along at least one axis 32 passing through a longitudinal axis 33 of the more than one protrusive element 16a, 16b.

Figure 2:
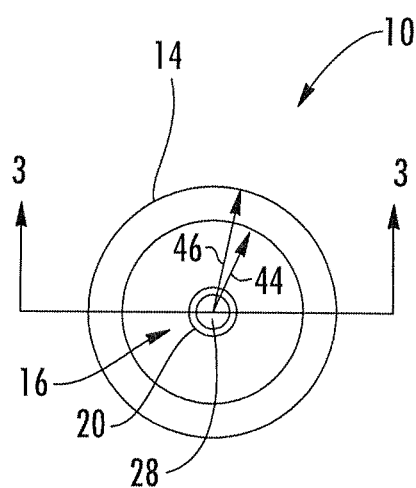
FIG. 2 is a bottom view of the exemplary medical instrument of FIG. 1, including cut line 3-3.
Figure 3:
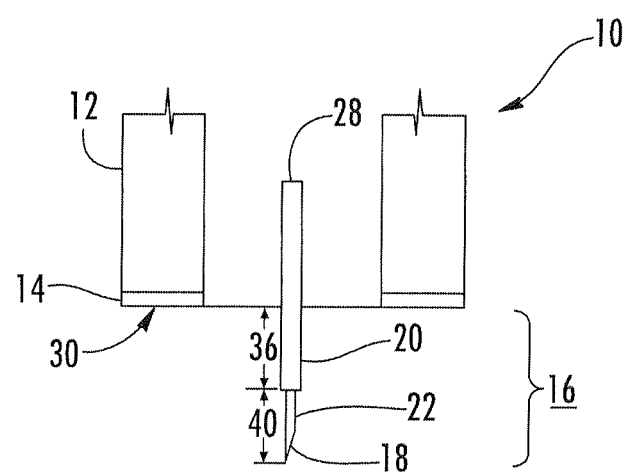
FIG. 3 is a cross-sectional view of the exemplary medical instrument of FIGS. 1 and 2 taken along cut line 3-3 in FIG. 2.

The ground plate 14 can have any number of possible shapes, including circle, ellipse, oval, triangle, and polygons, such as squares, pentagons, hexagons, heptagons, etc. The shape of the ground plate 14 can be such that the nanopulses create a generally symmetric electrical field around the first electrode 22. As shown in FIG. 2, the ground plate 14 can take the form of a ring having an inner radius 44 and an outer radius 46.

Figure 9:
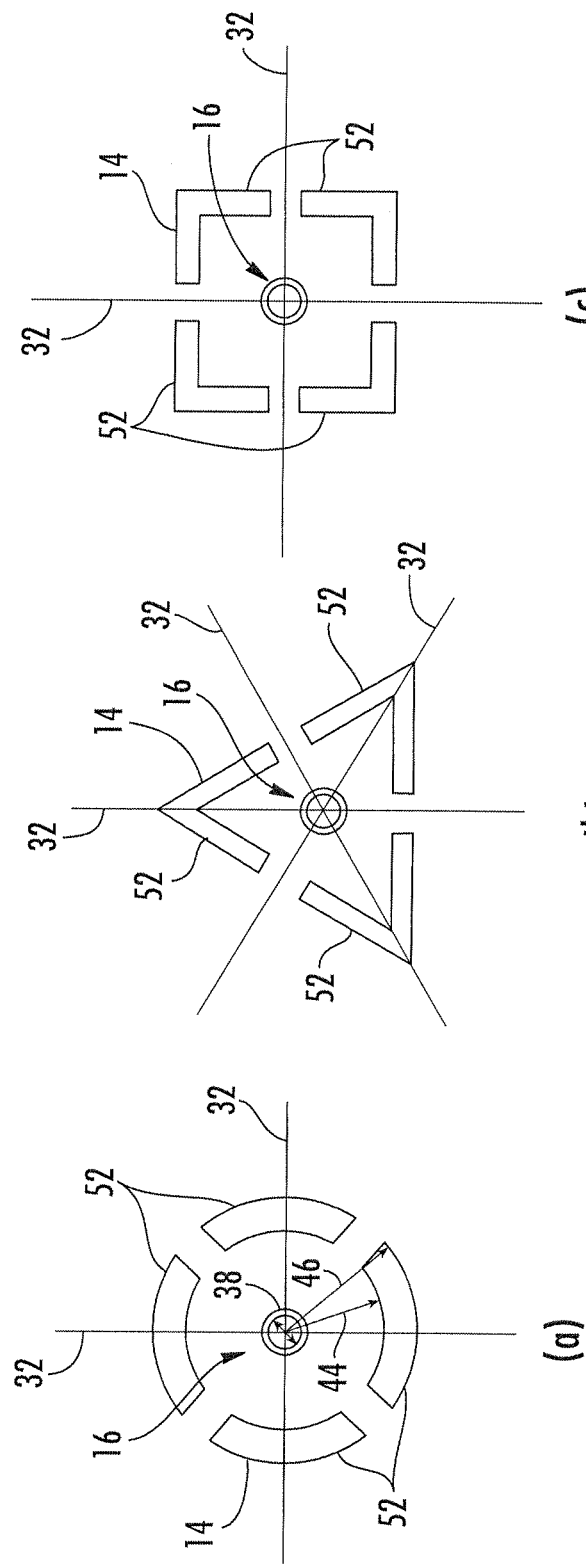
FIGS. 9(a)-(c) are bottom views of several exemplary geometries of the ground plate and the protrusive elements where the ground plate includes a plurality of ground plate segments.

As shown in FIGS. 9(a)-(c), the ground plate 14 can include a number of segments 52. At least one ground plate segment 52 can be electrically isolated from another ground plate segment 52 and at least two ground plate segments 52 can be connected to separate electrically conductive wires connected to a power supply 42. This configuration enables the at least two ground plate segments 52 and the first electrode(s) 22 to be energized simultaneously or separately at the same or different voltages.

Figure 10:
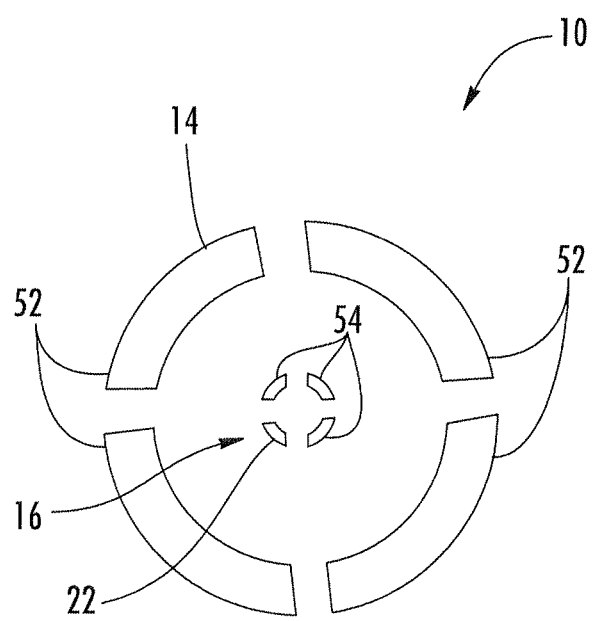
FIG. 10 is a bottom view of an exemplary geometry of the ground plate and first electrode, where the ground plate includes a plurality of ground plate segments and the first electrode includes a plurality of first electrode segments.

As shown in FIG. 10, the first electrode 22 can include a number of segments 54. At least one first electrode segment 54 can be electrically isolated from another first electrode segment 54 and at least two first electrode segments 54 can be connected to separate electrically conductive wires connected to a power supply 42. This configuration enables the at least two first electrode segments 54 and the ground plate 14 to be energized simultaneously or separately at the same or different voltages. The use of multiple, electrically isolated ground plate segments 52, multiple electrically isolated first electrode segments 54, or both, can be used to deliver highly controlled nsPEFs to different areas within a single treatment volume.

The protrusive element 16, the ground plate 14, or both 14, 16 can be replaceable. The protrusive element 16 and the ground plate 14 can be part of a single replaceable element or can be separate elements. The replaceable units can be removably attached to the medical instrument 10 using any attachment method compatible with medical usage. As an example, the luer lock and luer slip systems used for hypodermic needles can be used for attaching the protrusive element 16 and the ground plate 14 can be attached using a twist-on, snap-on, or other attachment system. Because the protrusive element 16 and the ground plate 14 may be replaced, a single medical instrument base can provide flexibility in terms of protrusive element geometry and ground plate geometry.

In some embodiments, the protrusive element 16, the ground plate 14, or both can be disposable. Because the protrusive element 16 comes into contact with bodily fluids during use, the ability to simply dispose of used protrusive elements 16 simplifies maintenance of a sterile environment that reduces the risk of infection or contamination.

The invention also includes a method of delivering electrotherapy to tissue. The method includes inserting the protrusive element 16 of the above-described medical instrument 10 for delivering electrotherapy through a tissue surface, e.g., the epidermis, into subsurface tissue 26 where the ground plate 14 can be contacting a tissue surface 24. The method can include applying a nanosecond pulse to create a voltage difference between the ground plate 14 and the first electrode 22 of about 1 to about 100 kV, or about 1 to about 70 kV, or about 1.5 to about 40 kV, or about 3 to about 30 kV or about 5 to about 30 kV, or about 10 to about 30 kV or about 15 to about 25 kV, or any combination thereof, e.g., about 1.5 to about 30 kV. The medical instrument 10 for delivering electrotherapy can be used to treat various conditions and target tissues including, but not limited to, tumors, such as carcinomas, lipomas, melanomas; cellulite; sweat glands; hair follicles; stem cells; fatty deposits; connective tissue and other conditions of the skin and subcutaneous tissues.

In such embodiments, the protrusive element 16 of the medical instrument 10 can be dimensioned such that the first electrode is adjacent to the target tissue. For example, the protrusive element 16 can penetrate the skin and into the subsurface tissue 26, here subcutaneous tissue, for treatment of a tumor. In another example, the protrusive element 16 can penetrate into the dermal layer for treatments targets at sweat glands or hair follicles.

Trials have demonstrated that nsPEF treatments can cause thermal injury to subcutaneous tissue, such as fiber septae 56. The pulsed electric field treatments can selectively damage fiber septae 56 in subsurface tissue 26, here adipose tissue, being treated. It is believed that the selective treatment is due to the orientation of the pulsed electrical field and the high conductivity of fiber septae relative to surrounding adipose tissue.

Figure 11:
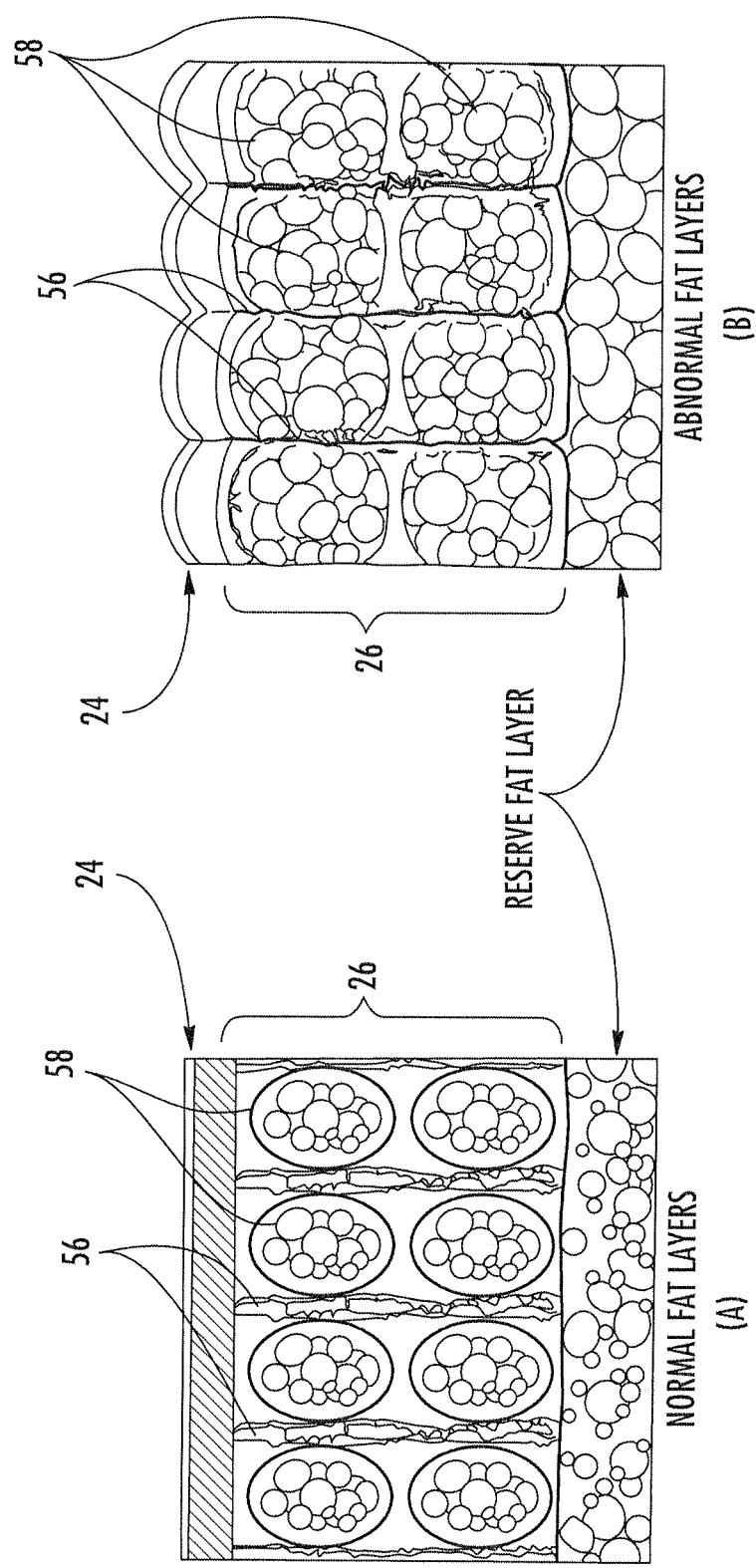
FIGS. 11(a) and (b) are cross-sectional views of skin and adipose tissue illustrating normal and abnormal fat layers, respectively.

Treatment of fiber septae 56, also known as septal tethers, or other connective tissues, using pulsed electric fields can reduce or eliminate dimpling of the skin caused by adipocyte lobules 58 held in tension by fiber septae 56 oriented perpendicular to the tissue surface 24. As shown in FIG. 11, when the adipocyte lobules 58 become enlarged, the fiber septae 56 cause the subsurface tissue 26, here adipose tissue, to dimple. The instrument for delivering nanosecond pulsed electric fields 10 can be used as part of a method to reduce dimpling of a tissue surface 24 by using the instrument 10 to apply pulsed electric fields to fiber septae 56 in subsurface tissue 26, here adipose tissue, below the tissue surface 24.

The method can include administering a plurality of nanosecond pulsed electric fields. The method can include administering at least 50 nsPEF pulses. The method can include administering a plurality of nanopulses designed to deliver a threshold total energy sufficient to treat a targeted tissue volume. The number of pulses can be modified during treatment based on real time current measurements, whereby the system calculates the total energy delivered and shuts off after reaching a preprogrammed threshold level of energy.

The nanosecond pulse can be 1 to 600 nanoseconds in duration, 10 to 400 nanoseconds in duration, 20 to 200 nanoseconds in duration, or 50 to 150 nanoseconds in duration. The peak power produced between the ground plate and the first electrode can be at least about 5 MW, at least about 7 MW or at least about 10 MW. The peak electrical field produced by the pulse can be at least about 1 kV/cm, at least about 5 kV/cm, at least about 10 kV/cm, or at least about 12 kV/cm. The temperature increase of the tissue proximate the first electrode caused by the nanosecond pulsed electric field can be about 1 degree Celsius or less, about 0.5 degree Celsius or less, about 0.25 degree Celsius or less, or about 0.01 degree Celsius or less.

Nanosecond-pulsed electric fields (nsPEFs) are extremely short in duration, high in electric field and power and low in energy. In contrast to electroporation, nsPEFs unexpectedly have effects on intracellular structures (such as the endoplasmic reticulum, nucleus, mitochondria, Golgi apparatus etc.) and functions as well as cell viability. For example, effects on cell viability can be lethal or non-lethal depending on the cell type and the nsPEF conditions. In addition, nsPEFs can have effects on the plasma membrane. However, the effects are specifically different than those observed in electroporation. Unexpectedly, nanosecond-pulsed electric fields can cause the formation of "nanopores" that are on the order of nanometers. Unlike electroporation, these nanopores allow the passage of ions, such as sodium, potassium, calcium, but not larger molecules such as drugs of DNA.

For example, in one example propidium iodide (PI) was used as a marker for "cell permeability." Propidium iodide has a molecular weight of 668 daltons and is about one (1) nanometer in diameter. As part of the study nsPEF conditions were manipulated to control whether PI could penetrate into cells treated by nsPEF.

In addition, nsPEFs introduced using a single needle electrode 10 described above have been shown to affect extracellular structures in adipose tissue, including collagen structures. Collagen is a protein secreted from a cell into the extracellular space. This is believed to be the first observation of pulsed electric field effects on structures that are not part of the cell. Thus, it would be possible for a single needle electrode 10 to deliver nsPEFs that effect other extracellular proteins and structures of the extracellular matrix.

The electrical fields produced by the devices disclosed herein have been modeled. Although not necessary for practicing the invention, the following discussion of the modeling results is included to provide insight into the instrument, system and method disclosed herein. These models are provided for illustrative purposes and should not be considered to limit the scope of inventive compositions and methods.

EXAMPLES

The dielectric relaxation time ($t_{RC}$) can be defined as:

$$t_{RC} = \frac{\varepsilon_0 \varepsilon_r}{\sigma} \quad (1)$$

where, $\varepsilon_0$ is the electric permittivity of free space (8.85× $10^{-12}$ F/m), $\varepsilon_r$ is the relative permittivity, and $\sigma$ is the conductivity. To model the electrical field in tissue, it was assumed that all the tissue properties were linear, which means that susceptibility is not a function of the E-field strength. Modeling was conducted at a frequency of 100 MHz and the dielectric properties of the relevant tissues were chosen as follows:

|  | Relative Permittivity | Conductivity (S/mn) |
|---|---|---|
| Adipose | 11 | 0.05 |
| Skin | 41 | 0.87 |
| Insulator | 2.1 | $10^{-6}$ |

The corresponding dielectric relaxation time ($t_{RC}$) at 100 MHz was calculated by using Eq. (1). The resulting dielectric relaxation time was 2 nanoseconds for adipose tissue and 0.5 nanoseconds for skin. Both of the times are much less than a pulse application time of 100 ns. Using these values, the predominant electrical field during the modeled nsPEF would be the conductive phase electrical field.

However, the dielectric properties of tissue are frequency dependent. For example, at 1 MHz, adipose tissue has a relative permittivity of 30 and a conductivity of 0.02 S/m. Using these values, the dielectric relaxation time ($t_{RC}$) is 13 nanoseconds. For lower frequency examples, the dielectric relaxation time is even longer.

The electrical field distribution modeling utilized MAGIC, a 3-D software which is based on Particle in Cell (PIC) leapfrog algorithm, and AMAZE-Precision. In order to simplify the modeling, the potential distribution for both the capacitive phase and the resistive phase were calculated separately.

Geometry of the Delivery Device

The single needle device used for the modeling can be represented by the medical instrument 10 is shown in FIG. 4. In the model, it was assumed that the geometry of the ground plate 14 was constant. The inner radius 44 of the ground plate 14 was 0.5 cm and the outer diameter 46 of the ground plate 14 was 1.4 cm. The diameter 38 of the needle 28 was 0.3 mm, i.e., a gauge 30 needle. In the modeling study, the length 40 of the first electrode 22, the length 36 of the electrical insulator 20, shown as shrink tubing, and the thickness of the tissue surface 24, shown as a skin layer, were varied to evaluate differences in electrical field distributions for different treatment conditions. The subsurface tissue 26, here adipose tissue, was assumed to have constant thicknesses of 1.5 cm. The model assumed a 21 kV rectangular pulse to the high voltage needle electrode 22 with the ground plate 14 at ground potential.

Modeling the Capacitive Phase

Figure 12:
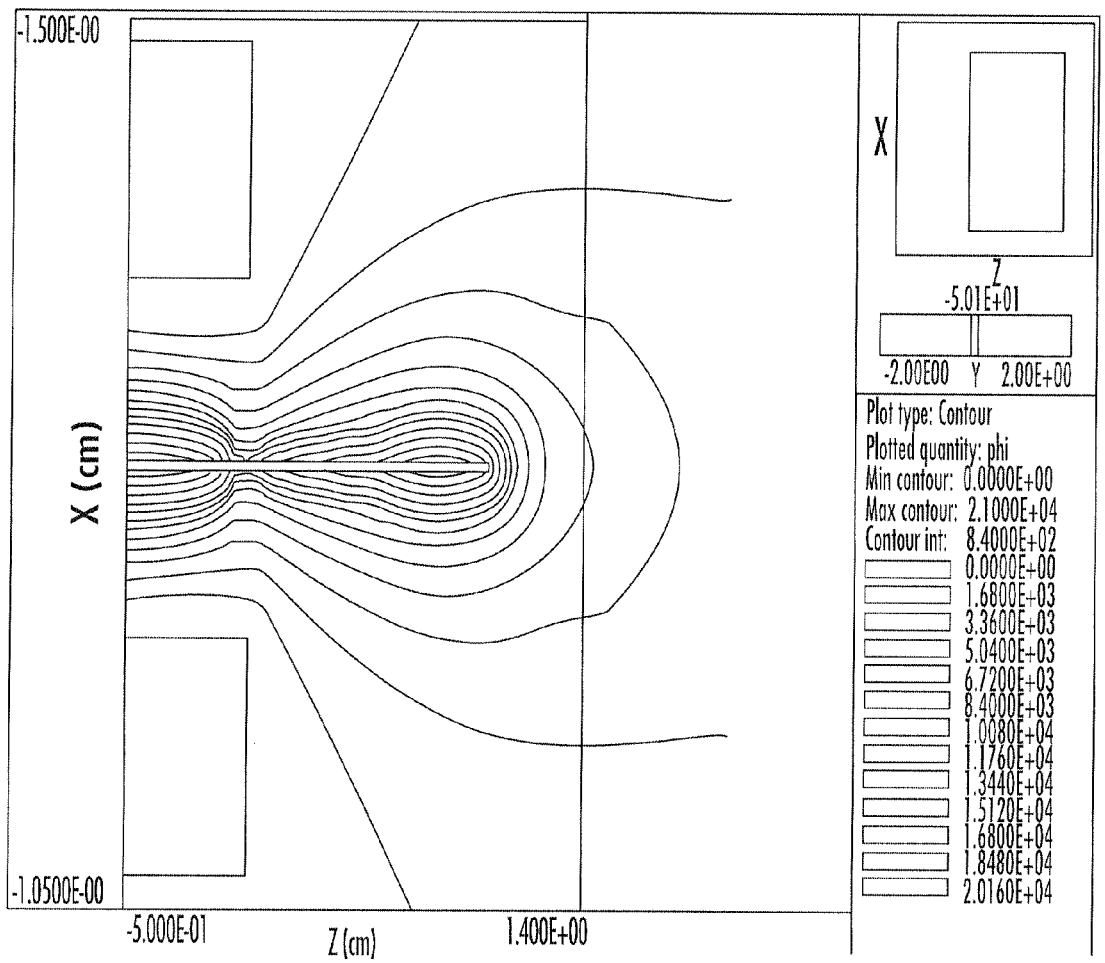
FIG. 12 is a graph showing the geometry used in the nsPEF modeling. In the figure, the equal-potential distribution is shown with the electrical field lines being perpendicular to the equal potential lines.

In nsPEF, the dielectric relaxation time is generally much less than the pulse application time. This is supported by the experimental observations that the pulse rises rapidly. Therefore modeling of the conductive phase was of interest. However, a review of the field distribution in the capacitive phase was of interest because the capacitive phase could cause the skin to suffer increased electrical stress. One result for the capacitive phase is shown in FIG. 12. The model that produced FIG. 12 was run assuming the needle was 1 cm long and was covered with a 0.7 cm shrink tubing insulator, leaving 0.3 cm of exposed first electrode 22. For purposes of modeling the capacitive phase, the thickness of tissue surface 24, i.e., skin thickness, was assumed to be 0.1 cm.

Figure 13A:
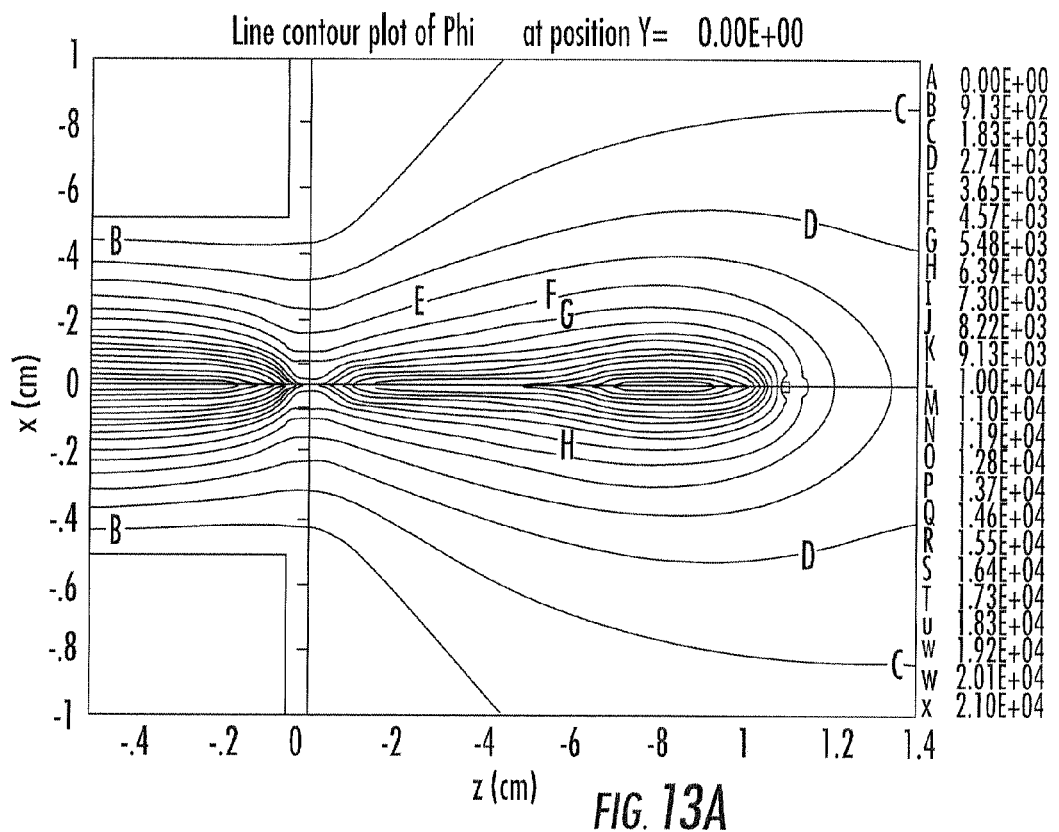
FIG. 13(a) is a graph of the potential distribution in the vicinity of the needle during the capacitive phase; and (b) is a graph of the electrical field distribution in the vicinity of the needle during the capacitive phase.
Figure 13B:
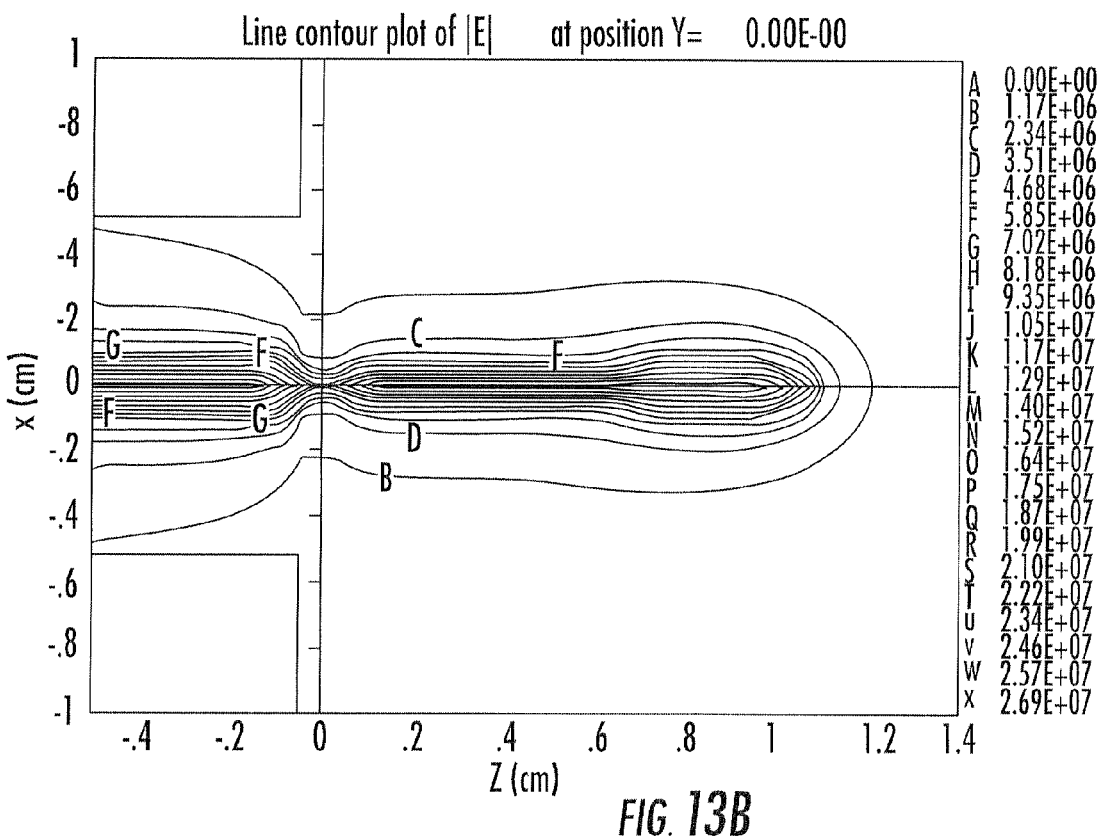

Due to capacitive coupling, the voltage not only appears in the needle insulator but also the surrounding tissues as shown in FIG. 13(a). But even in this early phase, a higher field distribution is observed at the exposed part of the needle, as shown in FIG. 13(b).

Modeling the Conductive Phase

The conductive phase was modeled using the conductivity values rather than the permittivity values of the tissue. As discussed previously, with pulses on the order of 100 nanosecond, the conductive phase is the dominant phase where the dielectric relaxation time is much less than the pulse application time. The modeling evaluated the influence of the needle insertion depth, shrink tubing length, and the thickness of the skin layer on the electrical field distribution for the parameters shown in the table below.

|  | Needle Length (cm) | Shrink Tubing Length (cm) | Length of First Electrode Exposed (cm) | Skin Thickness (cm) |
|---|---|---|---|---|
| Example 1 | 0.7 | 0.4 | 0.3 | 0.1 |
| Example 2 | 1.0 | 0.7 | 0.3 | 0.1 |
| Example 3 | 1.0 | 0.7 | 0.3 | 0.3 |

Example 1

Conductive Phase

Figure 14A:
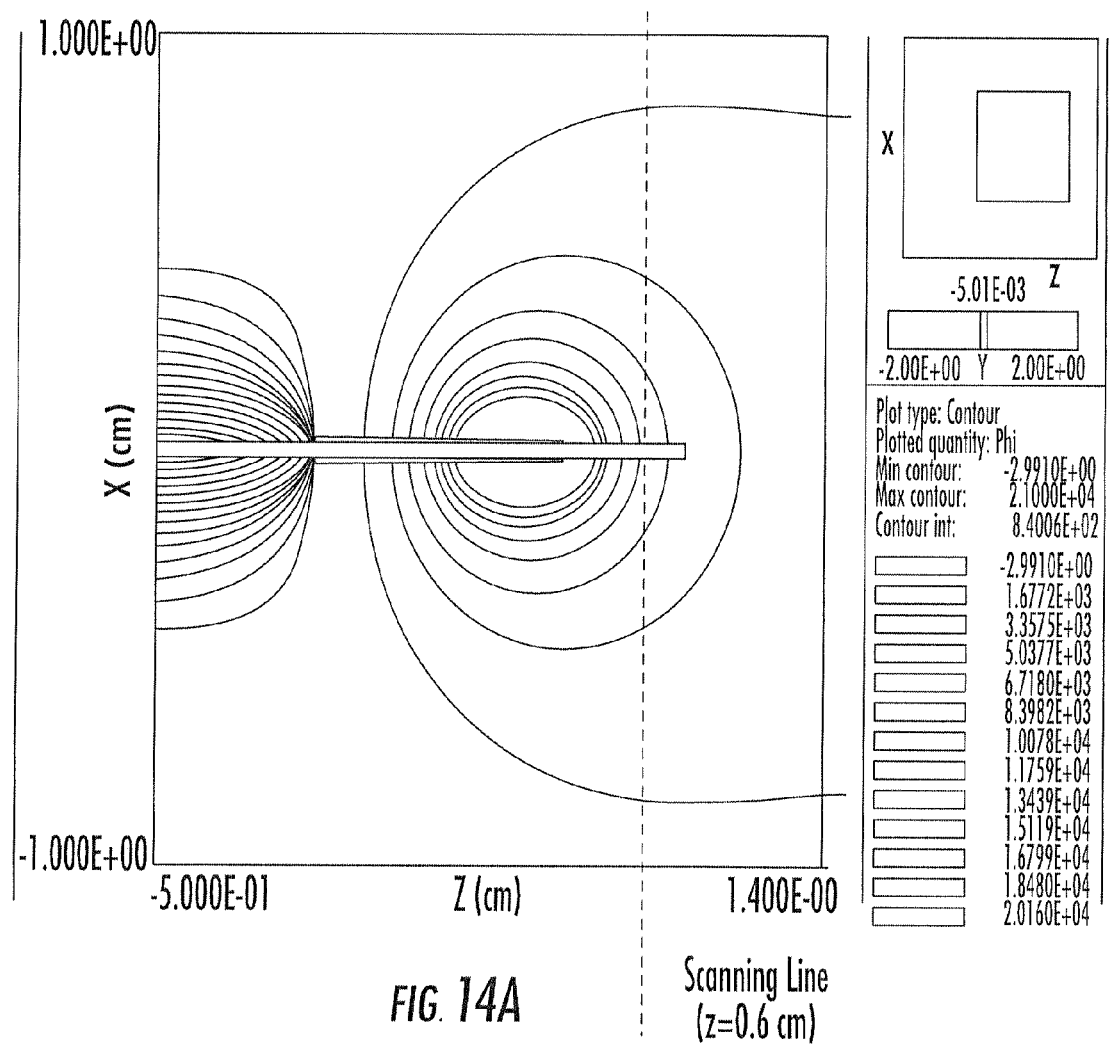
FIG. 14(a) is a graph of the conductive phase equal-potential distribution for Example 1; and (b) is a graph of the conductive phase electrical field distribution along the scanning line for Example 1.
Figure 15A:
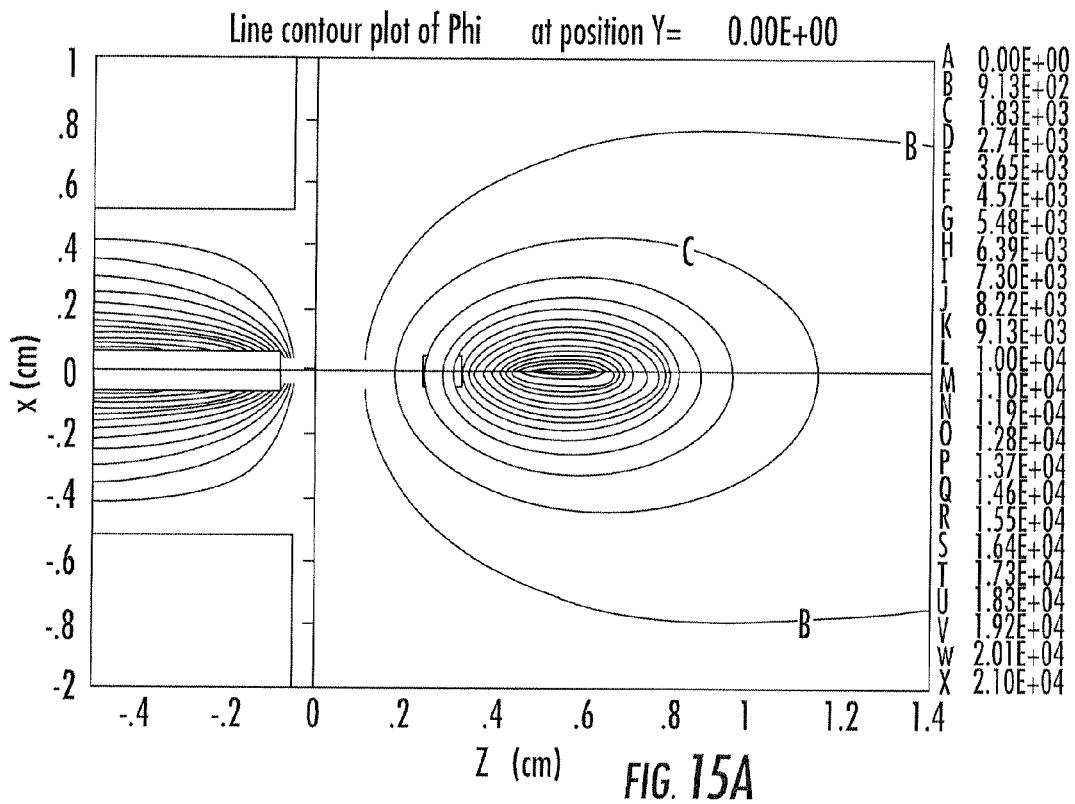
FIG. 15(a) is a graph of the conductive phase potential distribution in the vicinity of the needle for Example 1; and (b) is a graph of the conductive phase electrical field distribution in the vicinity of the needle for Example 1.

In Example 1, the 0.4 cm of the protrusive element 16 closest to the tissue surface 24 is coated with an electrically insulating material 20. Thus, when the protrusive element is inserted into the skin, the first electrode 22 begins 0.3 cm below the lowest extent of the skin and extends another 0.3 cm. FIGS. 14(a) and (b) show the equal-potential distribution and the electrical field distribution along the scanning line, respectively. FIGS. 15(a) and (b) show the potential distribution in the vicinity of the needle and the electrical field distribution in the vicinity of the needle, respectively.

Example 2

Conductive Phase

Figure 17A:
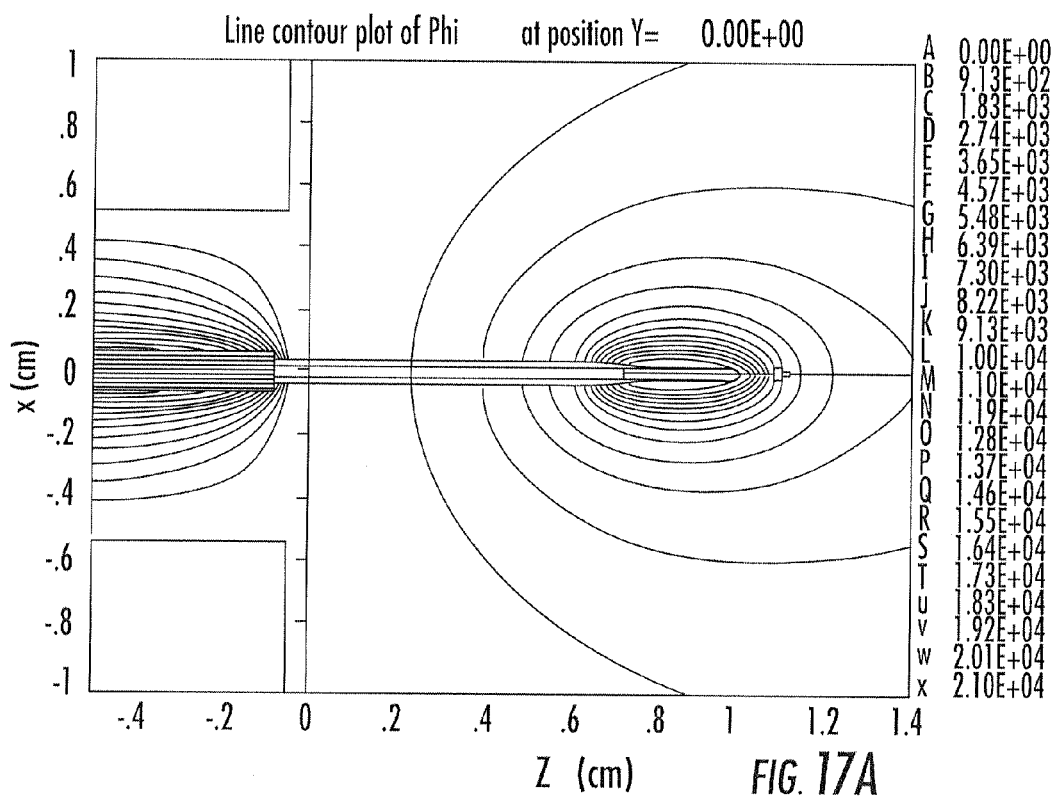
FIG. 17(a) is a graph of the conductive phase potential distribution in the vicinity of the needle for Example 2; and (b) is a graph of the conductive phase electrical field distribution in the vicinity of the needle for Example 2.

In Example 2, the 0.7 cm of the protrusive element 16 closest to the tissue surface 24 is coated with an electrically insulating material 20. Thus, when the protrusive element is inserted into the skin, the first electrode 22 begins 0.6 cm below the lowest extent of the skin and extends another 0.3 cm. FIGS. 16(a) and (b) show the equal-potential distribution and the electrical field distribution along the scanning line, respectively. FIGS. 17(a) and (b) show the potential distribution in the vicinity of the needle and the electrical field distribution in the vicinity of the needle, respectively.

Example 3

Conductive Phase

Figure 14B:
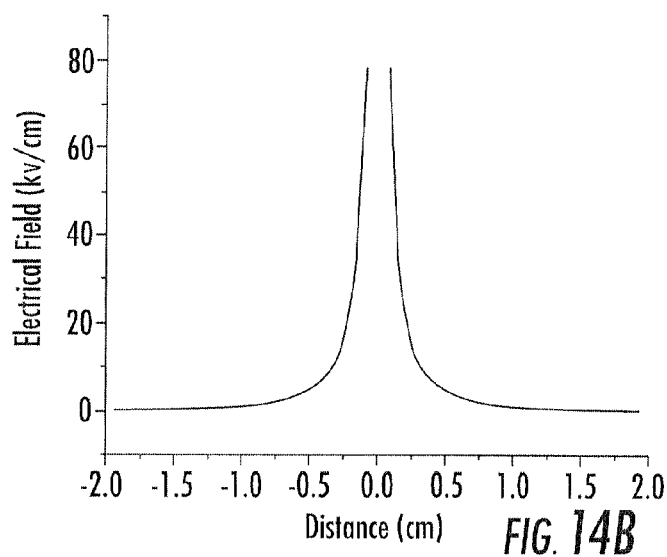
Figure 18A:
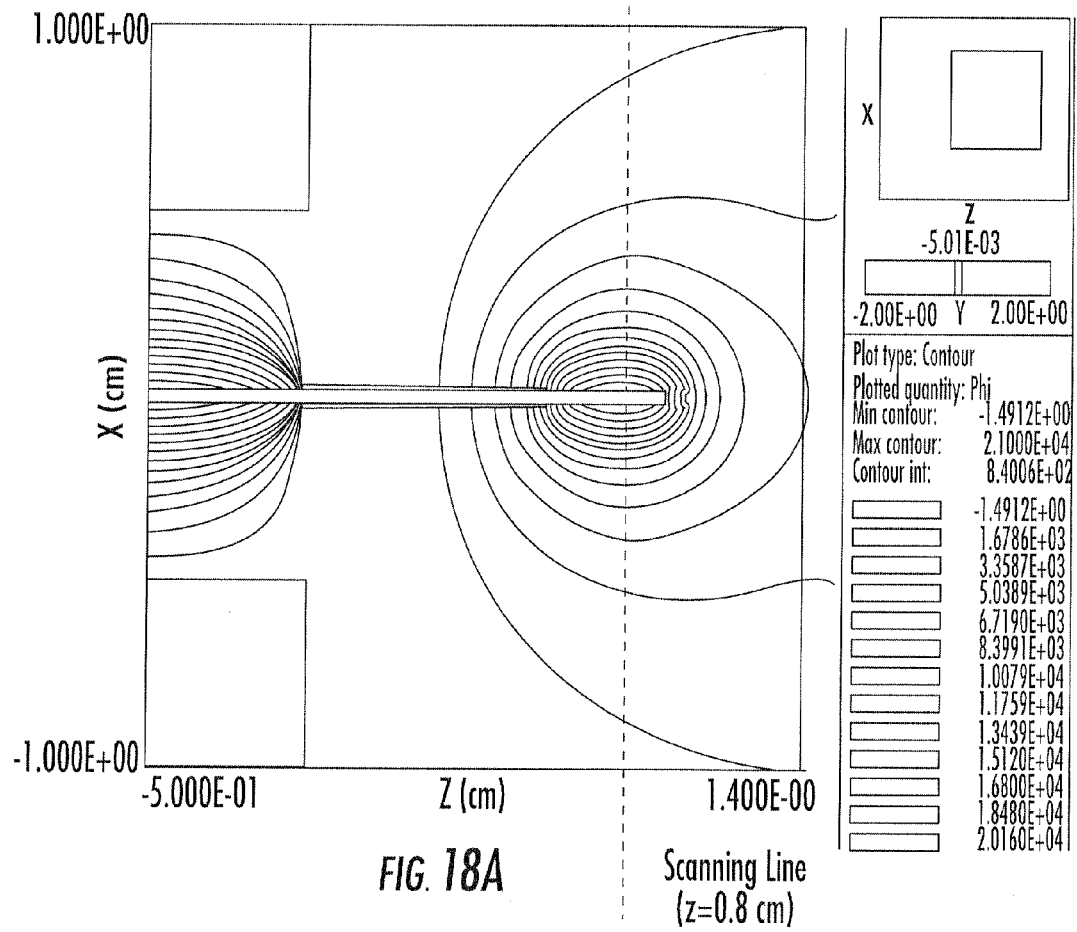
FIG. 18(a) is a graph of the conductive phase equal-potential distribution for Example 3; and (b) is a graph of the conductive phase electrical field distribution along the scanning line for Example 3.
Figure 18B:
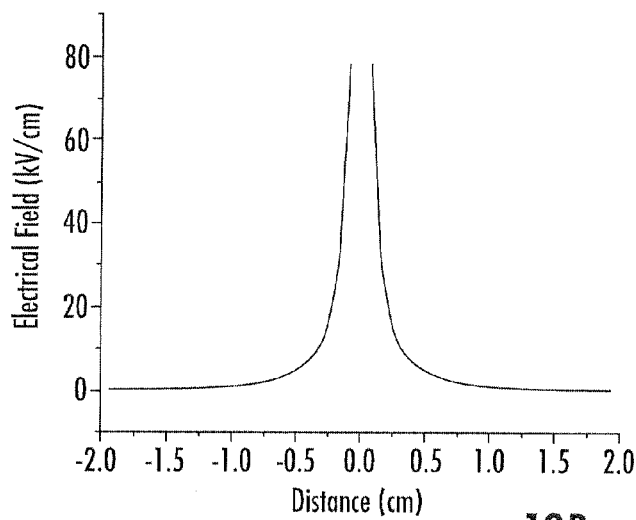
Figure 19A:
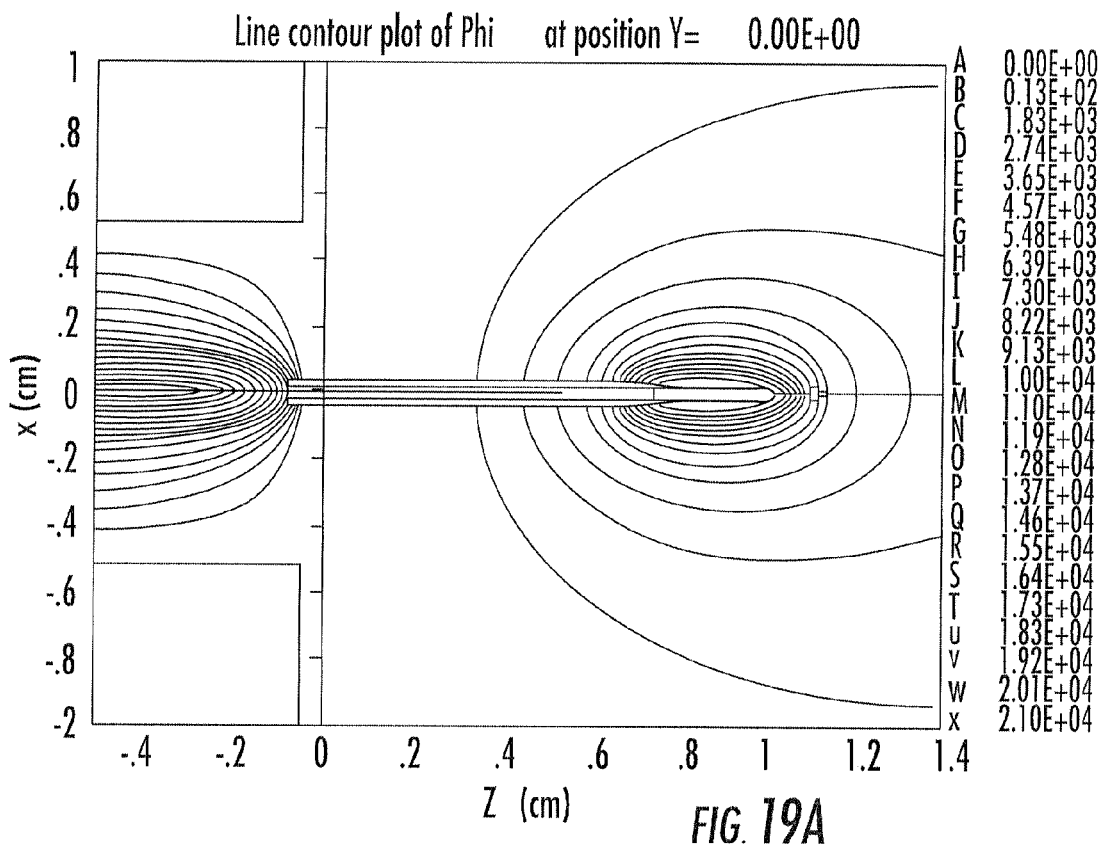
FIG. 19(a) is a graph of the conductive phase potential distribution in the vicinity of the needle for Example 3; and (b) is a graph of the conductive phase electrical field distribution in the vicinity of the needle for Example 3.

In Example 3, the 0.7 cm of the protrusive element 16 closest to the tissue surface 24 is coated with an electrically insulating material 20. Thus, when the protrusive element is inserted into the skin, the first electrode 22 begins 0.4 cm below the lowest extent of the skin and extends another 0.3 cm. FIGS. 18(a) and (b) show the equal-potential distribution and the electrical field distribution along the scanning line, respectively. FIGS. 19(a) and (b) show the potential distribution in the vicinity of the needle and the electrical field distribution in the vicinity of the needle, respectively Results The modeling results indicate that the electrical field can be localized in the vicinity of the first electrode. The electrical field decreases over a distance of 0.5 cm to about 1/10 of the value at the surface of the first electrode, as shown in FIG. 14(b), FIG. 16(b) and FIG. 18(b). The results explain how the inventive instrument, system and method can be used to deliver nsPEF without causing thermal or dielectric damage to the skin.

Figure 15B:
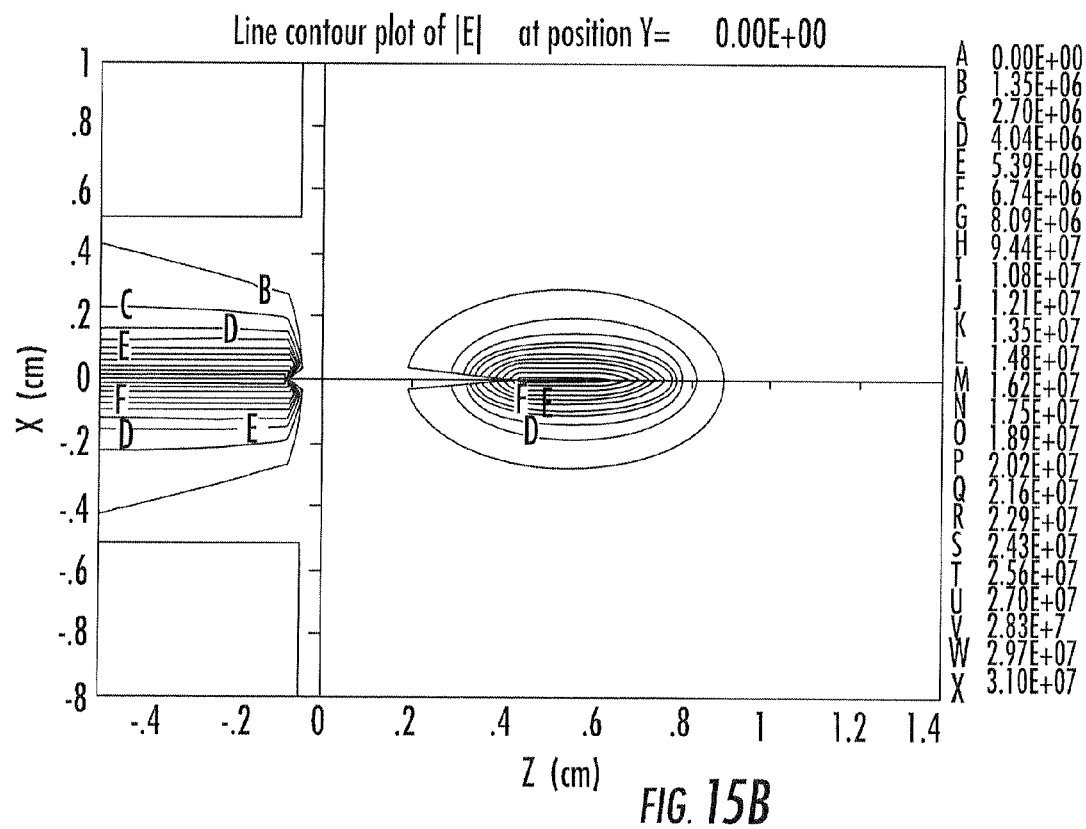
Figure 17B:
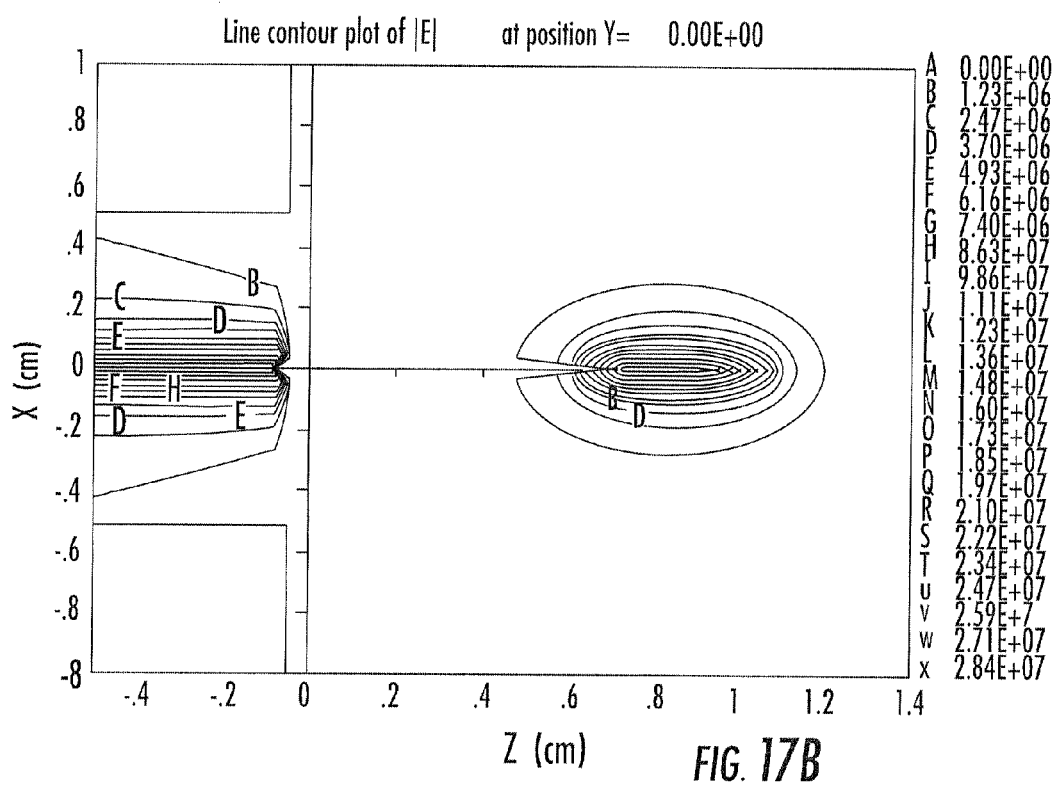

The electrical field amplitude appears to be independent from the insulation tubing length. This can be seen by comparing FIGS. 15(b) and 17(b). In Examples 1 and 2, the first electrode length was constant, but the needles had different insulation lengths and insertion depths. However, the electrical field distributions are almost identical. As shown in FIG. 15(b), e-field line B in Example 1 has an amplitude of 1.35E+6 (V/m). As shown in FIG. 17(b), e-field line B in Example 2 has a nearly identical amplitude of 1.23E+6 (V/m). As shown in FIGS. 15(b) and 17(b), the electrical field distributions of both Example 1 and Example 2 are in the form of similar "football" shaped volumes.

Figure 19B:
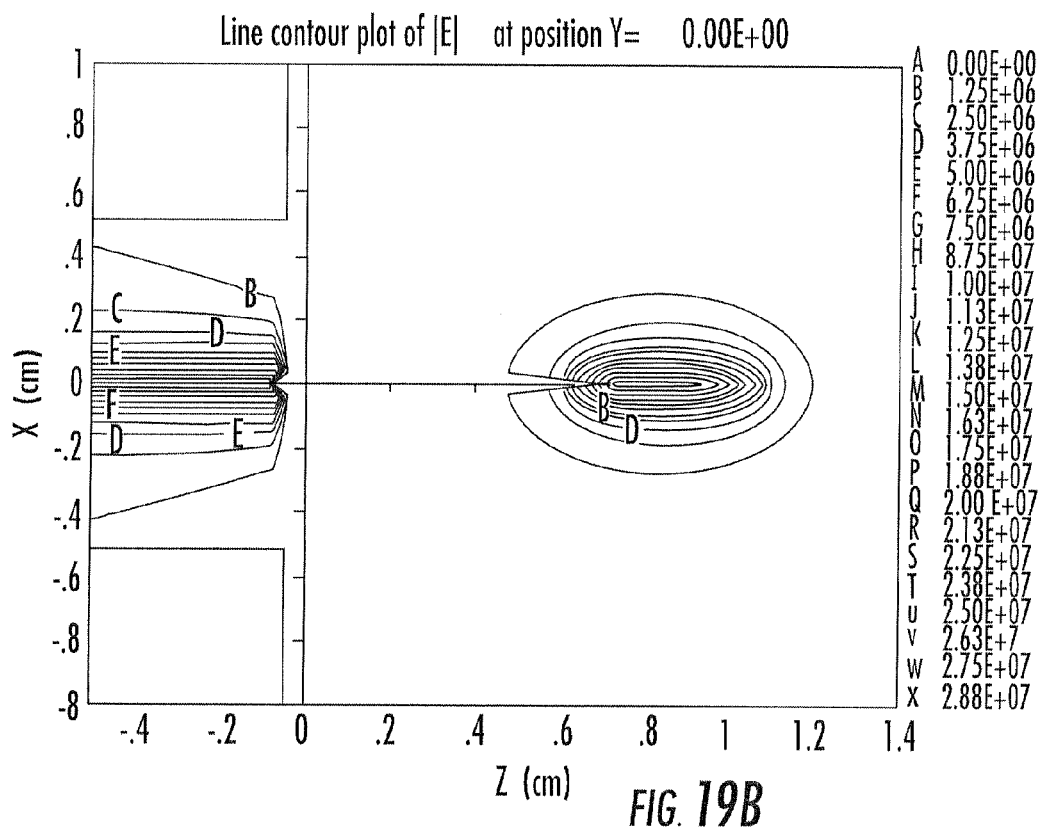

Using the same type of analysis, FIGS. 17(b) and 19(b) demonstrate that the thickness of the skin would not substantially influence the field distribution near the exposed portion of the first electrode.

Figure 20:
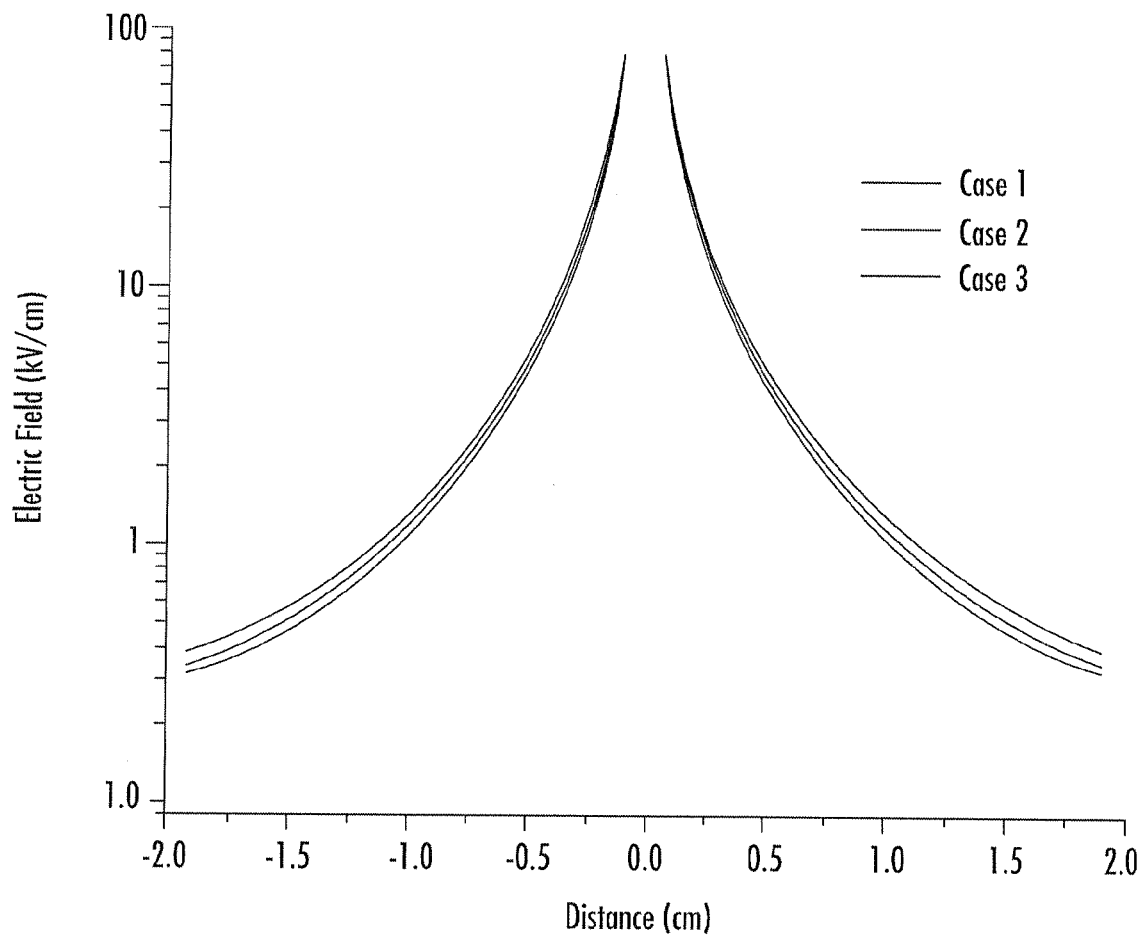
FIG. 20 is a graph of the conductive phase electrical field distribution in the vicinity of the needle.

The single needle ground plate device has a highly non-uniform electric field as demonstrated in the modeling. Most of the high field distribution is concentrated in the vicinity of the exposed needle. For a constant voltage but different insertion length, shrink tubing length and skin thickness, the electrical field decays in a very similar way over distance: it decreases over a distance of 0.5 cm to about 1/10 of the value at the needle surface, as shown in FIG. 20.

In the capacitive phase, the skin tissue is exposed to a slight electrical field. However, the generated pulses have a very fast risetime (<10 ns) which means the capacitive phase is much shorter compared to the conductive phase. This appears to allow the use of high voltage pulse that do not damage the skin. In the conductive phase, which is the dominant phase in the treatment, the insulator, i.e. adipose tissue, can hold the entire voltage and effectively protect the skin making the electrical field in the skin becomes negligible.

The foregoing is provided for purposes of illustrating, explaining, and describing embodiments of this invention. Modifications and adaptations to these embodiments will be apparent to those skilled in the art and may be made without departing from the scope or spirit of this invention.

The invention claimed is:

1. A medical instrument for delivering electrotherapy to tissue, comprising:
   an outer support member having a conductive plate at a distal end of the outer support member,
   wherein the conductive plate comprises a plurality of electrically isolated plate segments; and
   a plurality of protrusive elements, each having a tip that extends beyond the conductive plate,
   wherein each protrusive element comprises an electrically conductive material,
   wherein each protrusive element has a cylindrical, needle shape,
   wherein a first portion of each protrusive element proximate the conductive plate is coated with an electrical insulator and a second portion of each protrusive element proximate a distal end of each protrusive element comprises an electrode, wherein each electrode has a diameter of about 1 mm or less, wherein each electrode is from about 2 cm to about 4 cm in length, wherein each electrode comprises a plurality of parallel, adjacent, elongated electrode segments electrically isolated from one another along the lengths thereof, and wherein each protrusive element is designed to penetrate into tissue below a tissue surface while a tissue contacting surface of the conductive plate rests against the tissue surface, wherein each electrode segment and each plate segment is wired with a separate electrically conductive wire so that each electrode segment and each plate segment can be energized simultaneously or separately at the same or different voltages.

2. The medical instrument of claim 1, wherein each protrusive element, the conductive plate, or both are replaceable.

3. The medical instrument of claim 1, wherein the tissue contacting surface of the conductive plate is symmetric along at least one axis extending through and perpendicular to a longitudinal axis of each protrusive element.

4. The medical instrument of claim 1, wherein the tissue contacting surface of the conductive plate is symmetric along at least two different axes extending through and perpendicular to a longitudinal axis of each protrusive element.

5. The medical instrument of claim 1, wherein at least a portion of the tissue contacting surface of the conductive plate is free of electrically insulating coating materials.

6. The medical instrument of claim 1, wherein the first portion of each protrusive element, which acts as the electrical insulator, forms the majority of each protrusive element.

7. The medical instrument of claim 1, wherein each protrusive element extends from within a perimeter of the tissue contacting surface of the conductive plate.

8. The medical instrument of claim 1, wherein the tissue contacting surface of the conductive plate is a ring and each protrusive element extends from within the ring.

9. A system for delivering electrotherapy to subsurface tissue, comprising:
   a medical instrument for delivering electrotherapy, comprising
   an outer support member having a conductive plate at a distal end of the outer support member,
   wherein the conductive plate comprises a plurality of electrically isolated plate segments, and
   a plurality of protrusive elements, each having a tip that extends beyond the conductive plate,
   wherein each protrusive element comprises an electrically conductive material,
   wherein each protrusive element has a cylindrical, needle shape,
   wherein a first portion of each protrusive element proximate the conductive plate is coated with an electrical insulator and a second portion of each protrusive element proximate a distal end of each protrusive element comprises an electrode,
   wherein each electrode has a diameter of about 1 mm or less,
   wherein each electrode is from about 2 cm to about 4 cm in length,
   wherein each electrode comprises a plurality of parallel, adjacent, elongated electrode segments electrically isolated from one another along the lengths thereof,
   wherein each protrusive element is designed to penetrate into tissue below a tissue surface while a skin contacting surface of the conductive plate rests against the tissue surface; and
   a power supply coupled to said conductive plate and each electrode for applying electrical signals to provide electrotherapy to said subsurface tissue,
   wherein each electrode segment and each plate segment is wired with a separate electrically conductive wire so that each electrode segment and each plate segment can be energized simultaneously or separately at the same or different voltages.

10. The system of claim 9, wherein said power supply comprises a pulse generator.

11. A medical instrument for delivering electrotherapy to tissue, comprising:
   an outer support member having a conductive plate at a distal end of the outer support member,
   wherein the conductive plate comprises a plurality of electrically isolated plate segments; and
   a plurality of protrusive elements, each having a tip that extends beyond the conductive plate,
   wherein each protrusive element comprises an electrically conductive material,
   wherein each protrusive element has a cylindrical, needle shape,
   wherein a first portion of each protrusive element proximate the conductive plate is coated with an electrical insulator and a second portion of each protrusive element proximate a distal end of each protrusive element comprises an electrode,
   wherein each electrode has a diameter of about 1 mm or less,
   wherein each electrode comprises a plurality of parallel, adjacent, elongated electrode segments electrically isolated from one another along the lengths thereof, and
   wherein each protrusive element is designed to penetrate into tissue below a tissue surface while a tissue contacting surface of the conductive plate rests against the tissue surface,
   wherein the tissue contacting surface of the conductive plate is a ring and each protrusive element extends from within the ring, and
   wherein each electrode segment and each plate segment is wired with a separate electrically conductive wire so that each electrode segment and each plate segment can be energized simultaneously or separately at the same or different voltages.

12. A system for delivering electrotherapy to subsurface tissue, comprising:
   a medical instrument for delivering electrotherapy, comprising
   an outer support member having a conductive plate at a distal end of the outer support member,
   wherein the conductive plate comprises a plurality of electrically isolated plate segments, and
   a plurality of protrusive elements, each having a tip that extends beyond the conductive plate,
   wherein each protrusive element comprises an electrically conductive material,
   wherein each protrusive element has a cylindrical, needle shape,
   wherein a first portion of each protrusive element proximate the conductive plate is coated with an electrical insulator and a second portion of each protrusive element proximate a distal end of each protrusive element comprises an electrode, wherein each electrode has a diameter of about 1 mm or less, wherein each electrode comprises a plurality of parallel, adjacent, elongated electrode segments electrically isolated from one another along the lengths thereof, wherein each protrusive element is designed to penetrate into tissue below a tissue surface while a skin contacting surface of the conductive plate rests against the tissue surface;

wherein the tissue contacting surface of the conductive plate is a ring and each protrusive element extends from within the ring;

a power supply coupled to said conductive plate and each electrode for applying electrical signals to provide electrotherapy to said subsurface tissue, wherein each electrode segment and each plate segment is wired with a separate electrically conductive wire so that each electrode segment and each plate segment can be energized simultaneously or separately at the same or different voltages.

13. A method of delivering electrotherapy to subsurface tissue comprising:

using the medical device of claim 1 by inserting the plurality of protrusive elements of the medical device into subsurface tissue of a mammalian subject with the conductive plate contacting a tissue surface, and applying a pulse creating a voltage difference between the conductive plate and each of the electrodes of 1 kV to 100 kV.

14. The method of claim 13, wherein the pulse is about 100 picoseconds to about 1 microsecond in duration.

15. The method of claim 13, wherein a peak electrical field produced by the pulse is at least about 10 kV/cm.

16. The method of claim 13, wherein the pulses is applied to selectively target fiber septae or other connective tissues.

17. The method of claim 16, wherein the pulses is applied to reduce dimpling of the tissue surface.

* * * * *